United States Patent
Li et al.

(10) Patent No.: US 11,078,161 B2
(45) Date of Patent: Aug. 3, 2021

(54) ROCK-INHIBITING COMPOUND AND USES THEREOF

(71) Applicant: HITGEN INC., Sichuan (CN)

(72) Inventors: Jin Li, Sichuan (CN); Dengyou Zhang, Sichuan (CN); Jingchao Feng, Sichuan (CN); Wei Liao, Sichuan (CN); Li Lin, Sichuan (CN); Si Li, Sichuan (CN)

(73) Assignee: HITGEN INC., Chengdu (CN)

( * ) Notice: Subject to any disclaimer, the term of this patent is extended or adjusted under 35 U.S.C. 154(b) by 0 days.

(21) Appl. No.: 16/716,455

(22) Filed: Dec. 16, 2019

(65) Prior Publication Data

US 2020/0190035 A1 Jun. 18, 2020

Related U.S. Application Data

(63) Continuation of application No. PCT/CN2018/091161, filed on Jun. 13, 2018.

(30) Foreign Application Priority Data

Jun. 16, 2017 (CN) .......................... 201710459241.6

(51) Int. Cl.
  *C07D 217/02* (2006.01)
  *A61P 27/06* (2006.01)
  *C07D 401/12* (2006.01)
  *C07D 409/12* (2006.01)

(52) U.S. Cl.
  CPC ............ *C07D 217/02* (2013.01); *A61P 27/06* (2018.01); *C07D 401/12* (2013.01); *C07D 409/12* (2013.01)

(58) Field of Classification Search
  CPC .. C07D 217/02; C07D 401/12; C07D 409/12; A61P 27/06; A61P 25/00; A61P 27/00; A61P 27/02; A61K 31/472; A61K 31/4725
  See application file for complete search history.

(56) References Cited

U.S. PATENT DOCUMENTS

| 2009/0105231 A1* | 4/2009 | Sawada | A61P 31/12 |
| | | | 514/227.8 |
| 2009/0203690 A1* | 8/2009 | Akritopoulou-Zanze | |
| | | | A61P 25/28 |
| | | | 514/234.5 |
| 2011/0190341 A1* | 8/2011 | Plettenburg | A61P 25/08 |
| | | | 514/309 |
| 2014/0066453 A1* | 3/2014 | Blake | C07D 405/14 |
| | | | 514/253.04 |

FOREIGN PATENT DOCUMENTS

| CN | 101253152 A | 8/2008 | |
| CN | 101321748 A | 12/2008 | |
| CN | 102131784 A | 7/2011 | |
| CN | 109134433 * | 1/2019 | ........... A61K 31/551 |
| EP | 2002836 A1 * | 12/2008 | ........... C07D 471/16 |
| WO | WO-2007065916 A1 * | 6/2007 | ................ A61P 9/10 |
| WO | WO-2010056758 A1 * | 5/2010 | ........... C07D 403/04 |
| WO | WO-2019201296 A1 * | 10/2019 | ......... A61K 31/4725 |
| WO | WO-2020172615 A1 * | 8/2020 | ........... C07D 217/02 |

OTHER PUBLICATIONS

Ashton; Bioorg. Med. Chem. Lett. 2011,21,5191-5196. DOI:10.1016/j.bmcl.2011.07.056 (Year: 2011).*
Hu; Expert Opinion on Therapeutic Targets 2005, 9, 715-736. DOI: 10.1517/14728222.9.4.715 (Year: 2009).*
Tamura; Biochimica et Biophysica Acta 2005, 1754, 245-252. DOI:10.1016/j.bbapap.2005.06.015 (Year: 2005).*
Tonges; Brain 2012, 135, 3355-3370. DOI:10.1093/brain/aws254 (Year: 2012).*
Sturdivant; Bioorg Med Chem Lett, 2016, 26, 2475-2480. DOI: 10.1016/j.bmcl.2016.03.104 (Year: 2016).*
Extended European Search Report in Application EP 18818595, dated Feb. 11, 2021, 5 pages. (Year: 2021).*

* cited by examiner

*Primary Examiner* — Daniel R Carcanague

(57) ABSTRACT

Disclosed herein are a compound of formula (I) and a preparation method and uses thereof. The compound shows a good inhibitory activity against ROCK, providing a new medicinal strategy to clinically treat the diseases associated with abnormal ROCK activity.

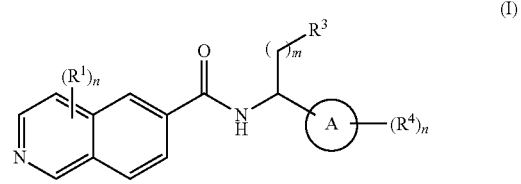

9 Claims, 3 Drawing Sheets

ROCK-INHIBITING COMPOUND AND USES THEREOF

CROSS-REFERENCE TO RELATED APPLICATIONS

This application is a continuation of International Patent Application No. PCT/CN2018/091161, filed on Jun. 13, 2018, which claims the benefit of priority from Chinese Patent Application No. 201710459241.6, filed on Jun. 16, 2017. The contents of the aforementioned applications, including any intervening amendments thereto, are incorporated herein by reference.

TECHNICAL FIELD

The present application relates to pharmaceutical synthesis, and more particularly to ROCK-inhibiting compounds and their uses in the treatment of ROCK-associated diseases.

BACKGROUND

Rho, pertaining to a small-molecule monopolymer GTPase superfamily, is a mammalian gene homolog and is capable of regulating the reorganization of the actin cytoskeleton through the most important downstream effector molecule Rho-associated coiled-coil containing protein kinase (ROCK), widely participating various biological processes such as cell cytoskeleton regulation, smooth muscle cell contraction, nerve regeneration, tumor cell infiltration and the regulation of cell apoptosis. After activated, the Rho/ROCK can be acted on various substrates to result in the occurrence of corresponding biological processes. Among them, the two primary substrates are myosin light chain (MLC) and myosin light chain phosphatase (MLCP), where the level of phosphorylation of MLC plays an important role in determining the degree of smooth muscle contraction. Specifically, the myosin light chain kinase (MLCK) is capable of phosphorylating Ser-19 of MLC to cause the contraction of smooth muscle, and the inhibition of MLCP can further enhance the phosphorylation of MLC and contraction of smooth muscle. The activated ROCK can phosphorylate the MLC itself to cause myofilament contraction, moreover, it can simultaneously inactivate the MLCP by phosphorylation to result in an increase in the level of the phosphorylation of MIX in the cytoplasm, indirectly promoting the myofilament contraction.

Based on the experiments performed on animal models, the Rho kinase activity inhibition shows many potential benefits to the treatment of human diseases, including cardiovascular diseases such as pulmonary arterial hypertension, hypertension, atherosclerosis, cardiac hypertrophy, intraocular hypertension and cerebral vasospasm, and central nervous system diseases such as neuronal degeneration. It has been found in a literature (involvement of Rho-kinase its hypertensive vascular disease: a novel therapeutic target in hypertension [J]. FASEB J., 2001, 15(6): 1062-4) that the expression and activity of ROCK are elevated in spontaneously hypertensive rats, indicating that ROCK is associated with the occurrence of hypertension in these animals. Moreover, it has also been demonstrated that a ROCK inhibitor Y-27632 is capable of significantly lowering the blood pressure of three types of hypertensive model rats (spontaneous hypertension, renal hypertension and deoxycorticosterone acetate-induced hypertension), but fails to show significant effects on the blood pressure of the control rats (Calcium sensitization of smooth muscle mediated by a Rho-associated protein kinase in hypertension [J]. Nature, 1997, 389(6654): 990-4). Another publication (Acute vasodilator effects of a Rho-kinase inhibitor, fasudil, in patients with severe pulmonary hypertension [J]. Heart, 2005: 91(3): 391-2) discloses that the ROCK inhibitors have a good therapeutic effect on pulmonary hypertension.

ROCK inhibitors that have been developed can be divided into five categories: (i) isoquinolines characterized by an isoquinoline structure and a piperazine ring connected therewith through a sulfonyl group; representative compound Fasudil (Uehata M, Ishizaki T, Satoh H, et al. Calcium sensitization of smooth muscle mediated by a Rho-associated protein kinase in hypertension [J]. Nature, 1997, 389: 990-994) and H-1152P (Tamura M. Nakao H, Yoshizaki H, et al. Development of specific Rho-kinase inhibitors and their clinical application [J]. Biochim Biophys Acta, 2005, 1754: 245-252) (ii) 4-aminopyridines containing a 4-aminopyridine nucleus, and cyclohexane or benzene ring at the center and a side chain at the 4-position of cyclohexane; representative compound Y-30141 (Takami A, Iwakubo M, Okada Y, et al. Design and synthesis of Rho kinase inhibitors [J]. Bioorg Med Chem, 2004, 12: 2115-2137); iii) indazoles having 5-amino or 5-alkoxy-1H indazole as a skeleton; iv) amide-urea inhibitors having a stranded structure formed by a phthalimide and a urea group; and v) other ROCK inhibitors; representative compound Rockout (Yarrow J C, Totsukawa G, Charras G T. et al. Screening for cell migration inhibitors via automated microscopy reveals a Rho-kinase inhibitor [J]. Chem Biol, 2005, 12: 385-395).

Currently, the commercially-available ROCK-inhibiting drugs mainly include Eril (Asahi Kasei Corporation) suitable for the treatment cerebral vasospasm and Glanatec® (K-115) (Kowa Co., Ltd) suitable for the treatment of intraocular hypertension and glaucoma, and the Glanatec® is only available in Japan. Therefore, it is of great social and economic significance to perform research and development on ROCK-targeting, small molecule drugs so as to produce a ROCK inhibitor with high bioactivity and selectivity, lasting potency, high stability, low toxic and side effects and low cost.

SUMMARY

In a first aspect, this application provides a compound of formula (I) or a stereoisomer thereof:

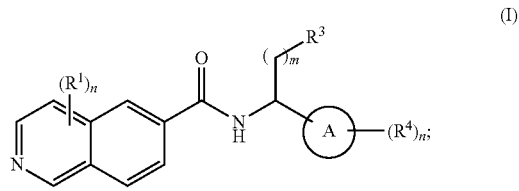

wherein:
n is independently 0, 1 or 2;
$R^1$ is independently selected from the group consisting of hydrogen, hydroxyl, halogen, amino, carboxyl, trifluoromethyl, nitro, cyano and $C_1$-$C_6$ alkyl;
m is, 0, 1, 2, 3, 4 or 5;
$R^3$ is —$NR^2R^{2'}$ or a substituted or unsubstituted N-containing heterocycloalkyl, wherein the substituted N-containing heterocycloalkyl comprises 1-2 substituents independently selected from the group consisting of halogen and $C_1$-$C_6$ alkyl;

R² and R²' are independently selected from the group consisting of hydrogen and $C_1$-$C_6$ alkyl;

A ring is selected from the group consisting of 5- to 6-membered aromatic ring, 5- to 6-membered heteroaromatic ring and

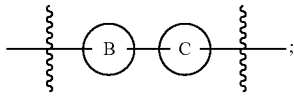

wherein B ring and C ring are independently selected from the group consisting of 5- to 6-membered aromatic ring and 5- to 6-membered heteroaromatic ring;

$R^4$ is each independently selected from the group consisting of hydrogen, halogen, nitro, cyano, $C_1$-$C_6$ alkyl, $C_2$-$C_6$ alkenyl, $C_2$-$C_6$ alkynyl, 3- to 6-membered cycloalkyl, 3- to 6-membered heterocycloalkyl, —$(CH_2)_mOR^a$, —$(CH_2)_mOC(O)R^a$, —$(CH_2)_mOC(O)NR^aR^b$, —$(CH_2)_mNR^aR^b$, —$(CH_2)_mNR^aC(O)r^b$, —$(CH_n)_mNR^aC(O)OR^b$, —$(CH_2)_mC(O)R^a$, —$(CH_2)_mC(O)OR^a$ and —$(CH_2)_mC(O)NR^aR^b$; and $R^a$ and $R^b$ are independently selected from the group consisting of hydrogen, $C_1$-$C_6$ alkyl, $C_2$-$C_6$ alkenyl, $C_2$-$C_6$ alkynyl, substituted and unsubstituted 3- to 6-membered cycloalkyl, substituted and unsubstituted 3- to 6-membered heterocycloalkyl, substituted and unsubstituted 5- to 6-membered aromatic ring and substituted and unsubstituted 5- to 6-membered heteroaromatic ring, wherein the substituted 3- to 6-membered cycloalkyl, substituted 3- to 6-membered heterocycloalkyl, substituted 5- to 6-membered aromatic ring and substituted 5- to 6-membered heteroaromatic ring each comprises 1-2 substituents independently selected from the group consisting of halogen and $C_1$-$C_6$ alkyl.

In an embodiment, $R^3$ is a 4- to 5-membered N-containing heterocycloalkyl.

In an embodiment, in the case that $R^3$ is an N-containing heterocycloalkyl and A ring is substituted with two $R^4$ groups, the two $R^4$ groups are not simultaneously halogen.

In an embodiment, the compound is shown as formula (II):

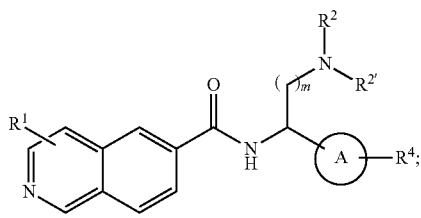

(II)

wherein:

$R^1$ is selected from the group consisting of hydrogen, hydroxyl, halogen, amino, carboxyl, trifluoromethyl, nitro, cyano and $C_1$-$C_6$ alkyl;

m is 0, 1, 2 or 3;

$R^2$ and $R^{2'}$ are independently selected from the group consisting of hydrogen and $C_1$-$C_6$ alkyl;

A ring is selected from the group consisting of 5- to 6-membered aromatic ring, 5- to 6-membered heteroaromatic ring and

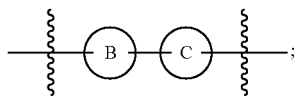

wherein B ring and C ring are independently selected from the group consisting of 5- to 6-membered aromatic ring and 5- to 6-membered heteroaromatic ring;

$R^4$ is selected from the group consisting of hydrogen, halogen, nitro, cyano, $C_1$-$C_6$ alkyl, $C_2$-$C_6$ alkenyl, $C_2$-$C_6$ alkynyl, 3- to 6-membered cycloalkyl, 3- to 6-membered heterocycloalkyl, —$(CH_2)_mOR^a$, —$(CH_2)_mOC(O)R^a$, —$(CH_2)_mOC(O)NR^aR^b$, —$(CH_2)_mNR^aR^b$, —$(CH_2)_mNR^aC(O)R^b$, —$(CH_2)_mNR^aC(O)OR^b$, —$(CH_2)_mC(O)R^a$, —$(CH_2)_mC(O)OR^a$ and —$(CH_2)_mC(O)NR^aR^b$; and $R^a$ and $R^b$ are independently selected from the group consisting of hydrogen, $C_1$-$C_6$ alkyl, $C_2$-$C_6$ alkenyl, $C_2$-$C_6$ alkynyl, substituted and unsubstituted 3- to 6-membered cycloalkyl, substituted and unsubstituted 3- to 6-membered heterocycloalkyl, substituted and unsubstituted 5- to 6-membered aromatic ring and substituted and unsubstituted 5- to 6-membered heteroaromatic ring, wherein the substituted 3- to 6-membered cycloalkyl, substituted 3- to 6-membered heterocycloalkyl, substituted 5- to 6-membered aromatic ring and substituted 5- to 6-membered heteroaromatic ring each comprises 1-2 substituents independently selected from the group consisting of halogen and $C_1$-$C_6$ alkyl.

In an embodiment, the compound is selected from the group consisting of:

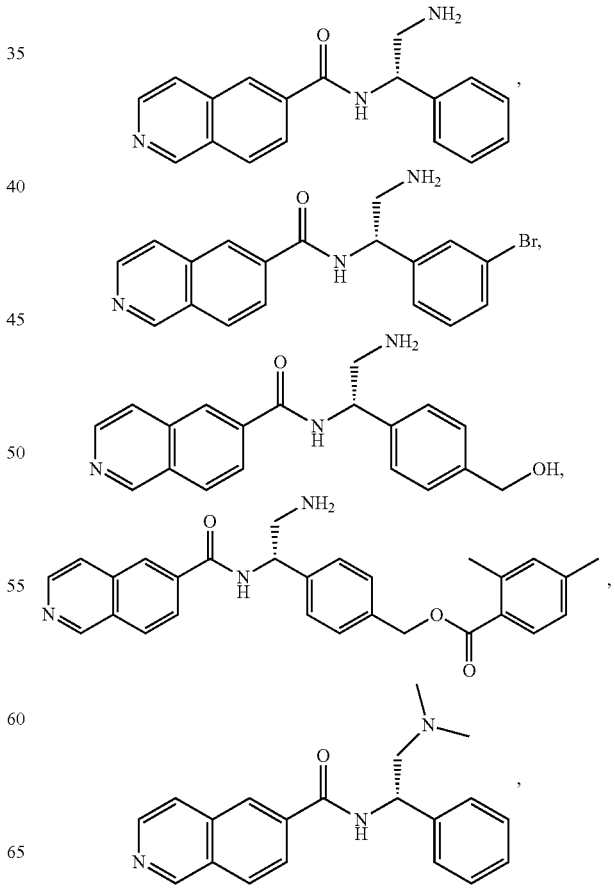

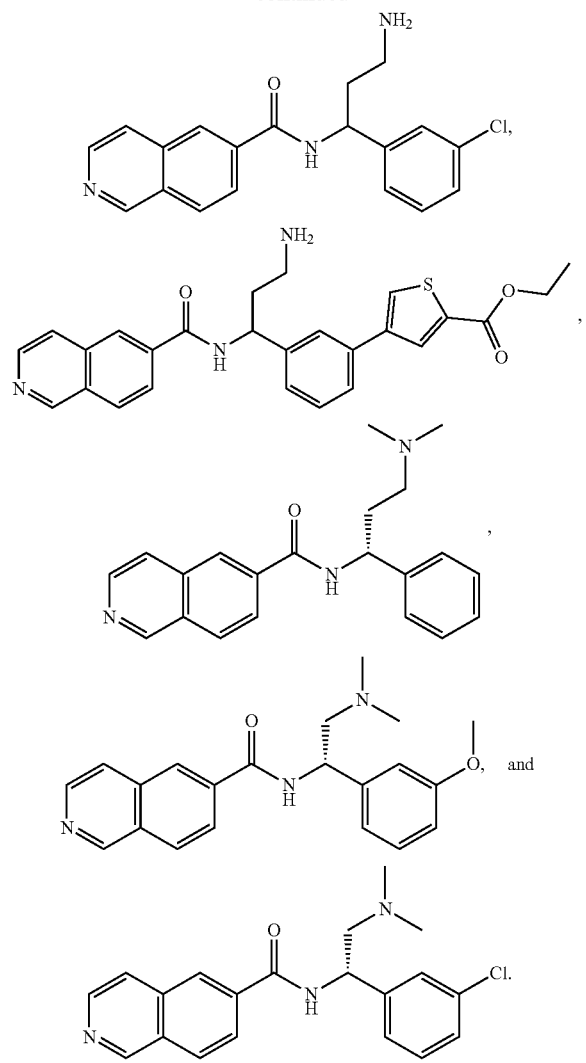

In an embodiment, the compound is shown as formula (III):

(III)

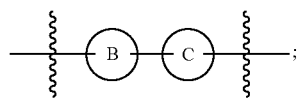

wherein:

R$^1$ is selected from the group consisting of hydrogen, hydroxyl, halogen, amino, carboxyl, trifluoromethyl, nitro, cyano and C$_1$-C$_6$ alkyl;

m is 0, 1, 2 or 3;

A ring is selected from the group consisting of 5- to 6-membered aromatic ring, 5- to 6-membered heteroaromatic ring and

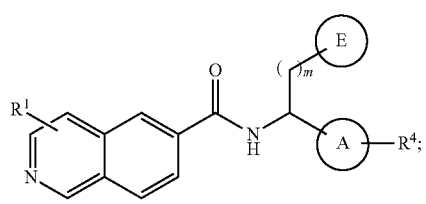

wherein B ring and C ring are independently selected from the group consisting of 5- to 6-membered aromatic ring and 5- to 6-membered heteroaromatic ring;

E ring is a substituted or unsubstituted N-containing heterocycloalkyl, wherein the substituted N-containing heterocycloalkyl comprises 1-2 substituents independently selected from the group consisting of halogen and C$_1$-C$_6$ alkyl;

R$^4$ is selected from the group consisting of hydrogen, halogen, nitro, cyano, C$_1$-C$_6$ alkyl, C$_2$-C$_6$ alkenyl, C$_2$-C$_6$ alkynyl, 3- to 6-membered cycloalkyl, 3- to 6-membered heterocycloalkyl, —(CH$_2$)$_m$OR$^a$, —(CH$_2$)$_m$OC(O)R$^a$, —(CH$_2$)$_m$OC(O)NR$^a$R$^b$, —(CH$_2$)$_m$NR$^a$R$^b$, —(CH$_2$)$_m$NR$^a$C(O)R$^b$, —(CH$_2$)$_m$NR$^a$C(O)OR$^b$, —(CH$_2$)$_m$C(O)R$^a$, —(CH$_2$)$_m$C(O)OR$^a$ and —(CH$_2$)$_m$C(O)NR$^a$R$^b$; and R$^a$ and R$^b$ are independently selected from the group consisting of hydrogen, C$_1$-C$_6$ alkyl, C$_2$-C$_6$ alkenyl, substituted and unsubstituted 3- to 6-membered cycloalkyl, substituted and unsubstituted 3- to 6-membered heterocycloalkyl, substituted and unsubstituted 5- to 6-membered aromatic ring and substituted and unsubstituted 5- to 6-membered heteroaromatic ring, wherein the substituted 3- to 6-membered cycloalkyl, substituted 3- to 6-membered heterocycloalkyl, substituted 5- to 6-membered aromatic ring and substituted 5- to 6-membered heteroaromatic ring each comprises 1-2 substituents independently selected from the group consisting of halogen and C$_1$-C$_6$ alkyl.

In an embodiment, the E ring is a 4- to 5-membered N-containing heterocycloalkyl.

In an embodiment, the compound is selected from the group consisting of

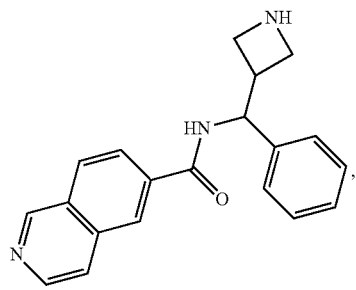

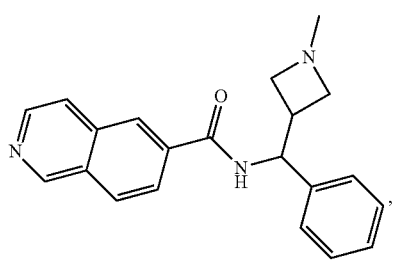

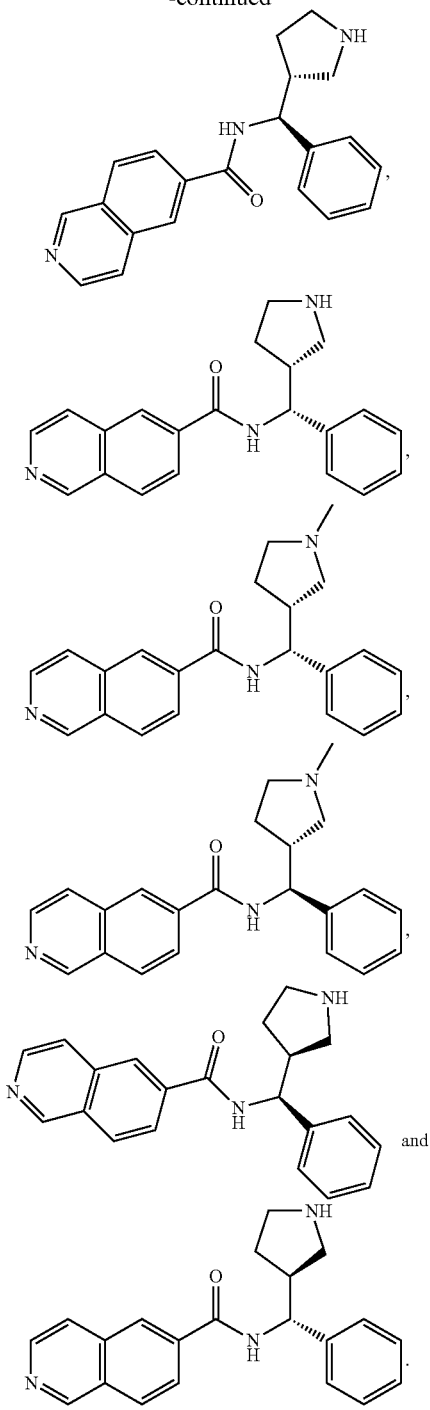

In a second aspect, this application provides a method of treating a disease associated with abnormal ROCK activity in a patient in need thereof, comprising:

administering an effective amount of the above compound, or a stereoisomer, a crystal, a pharmaceutically acceptable salt, a hydrate or a solvate thereof to the patient.

In an embodiment, the disease associated with abnormal ROCK activity is associated with cytoskeleton regulation, smooth muscle contraction and nerve regeneration.

In an embodiment, the disease associated with abnormal ROCK activity is ocular hypertension or glaucoma.

In a third aspect, this application provides a pharmaceutical composition, comprising the above compound, or a stereoisomer, a crystal, a pharmaceutically acceptable salt, a hydrate or a solvate thereof as an active ingredient and a pharmaceutically acceptable adjuvant.

The compounds provided herein and derivatives thereof can be named according to the IUPAC (International Union of Pure and Applied Chemistry) or CAS (Chemical Abstracts Services, Columbus, Ohio) naming system.

Unless otherwise specified, the initial definitions of a group or term used herein apply to that group or term throughout the specification. For terms without being specifically defined herein, those skilled in the art can understand their definitions based on the contents disclosed herein.

As used herein, term "substitution" means that one or more hydrogen atoms in a molecule are substituted with other different atoms or groups.

The minimum and maximum numbers of carbon atoms in a hydrocarbon group are indicated by a prefix, for example, a $C_{a-b}$ alkyl indicates any alkyl group containing "a" to "b" carbon atoms. Therefore, for example, a $C_{1-4}$ alkyl refers to an alkyl containing 1-4 carbon atoms.

As used herein, term "alkenyl" refers to the presence of one or more carbon-carbon double bonds, and term "alkynyl" refers to the presence of one or more carbon-carbon triple bonds.

As used herein, terms "$C_{a-b}$ alkoxy group", "$C_{a-b}$ carbalkoxyl", "alkylamino" and "$C_{a-b}$ alkanoyl" refer to a group formed through the linking of an alkyl containing "a" to "b" carbon atoms respectively to an oxygen atom, an ester group, an amino group and an acyl group.

The stereoisomer mentioned herein includes enantiomer and diastereomer.

The halogen used herein includes fluorine atom, chlorine atom, bromine atom and iodine atom.

The hetero atom mentioned herein includes nitrogen atom, oxygen atom and sulfur atom.

As used herein, term "cycloalkyl" refers to a non-aromatic cyclic hydrocarbon group, including saturated cycloalkyl and partially saturated cycloalkyl.

As used herein, term "heterocycloalkyl" refers to a non-aromatic cycloalkyl containing a heteroatom in the ring, including saturated heterocycloalkyl and partially saturated heterocycloalkyl.

As used herein, term "aromatic ring" refers to a cyclic hydrocarbon group having aromaticity.

As used herein, term "heteroaromatic ring" refers to an aromatic ring containing a hetero atom in the ring.

As used herein, term "pharmaceutically acceptable" means that a carrier, a supporter, a diluent and an excipient and/or salts thereof are generally chemically or physically compatible with the other ingredients in the pharmaceutical preparation, and are physiologically compatible with the recipient.

As used herein, terms "salt" and "pharmaceutically acceptable salt" refer to a salt formed by the above-mentioned compound or stereoisomers thereof with an organic and/or inorganic acid and/or base, including acid salt, basic salt, zwitterionic salt (inner salt) and quaternary ammonium salt (such as alkylammonium salt). These salts can be directly obtained in the final separation and purification of die compound of the invention, and can be also prepared by mixing the above compound or a stereoisomer thereof with an appropriate amount (such as equal equivalent) of an acid or a base. Specifically, these salts may be precipitated and collected by filtration, or recovered after evaporation of the solvent, or prepared by lyophilization. The salt described herein may be a hydrochloride, sulfate, citrate, benzenesulfonate, hydrobromide, hydrofluorate, phosphate, acetate, propionate, fumarate, maleate, tartrate or trifluoroacetate of the compound.

In some embodiments, the compounds of the invention can be used in combination with each other, or used in combination with any other active agents to prepare a medication or a pharmaceutical composition for regulating cell function or treating a disease. In the case of using a group of compounds, these compounds can be simultaneously, separately or sequentially administered to the subject.

Obviously, based on the common technical knowledge and conventional means in the art, various modifications, replacements and variations can be made without departing from the spirit of the invention, which should fall within the scope of the invention.

The invention will be further described below with reference to the embodiments, and these embodiments are not intended to limit the invention.

DETAILED DESCRIPTION OF EMBODIMENTS

Figure 1:
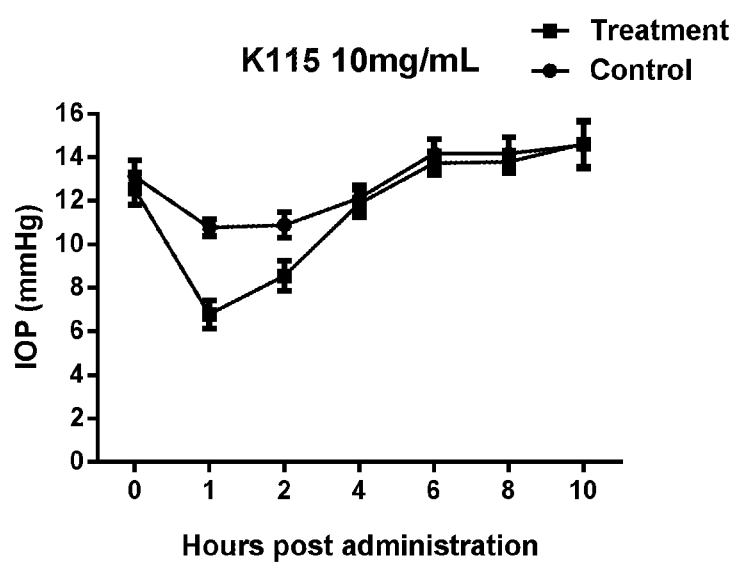
FIG. 1 shows the experimental results of the intraocular pressure-lowering activity of K115 on New Zealand rabbits with normal intraocular pressure.

Compounds are determined by nuclear magnetic resonance (NMR) and mass spectrometry (MS) for the structure, where in the NMR analysis, the NMR shift (δ) is expressed by a unit of ppm ($10^{-6}$); nuclear magnetic instruments (Bruker AvanceIII 400 and Bruker Avance 300) are employed; die solvents include DMSO-d6, CDCl$_3$ and MeOD; and tetramethylsilane (TMS) is adopted as an internal standard.

LC-MS analysis is performed on Shimadzu LC-MS 2020 (ESI).

HPLC analysis is performed using Shimadzu LC-20A.

MPLC (medium pressure preparative liquid chromatography) is performed using a Gilson GX-281 reversed-phase preparative chromatograph.

Column chromatography generally employs 200-300 mesh silica gel (Yantai Huanghai Co.) as the carrier.

Thin-layer chromatography employs HSGF254 (Yantai Huanghai Co.) or GF254 (Qingdao Haiyang Co.) silica gel plate with a thickness of 0.4-0.5 mm.

The raw materials and equipments used herein are all commercially available. Some known starting materials can be synthesized using the methods known in the art, or purchased from manufactures such as Energy Chemical Co., Chengdu Kelong Chemical Co., Ltd., Accela ChemBio Co., Ltd. and J&K Scientific Ltd.

Reactions are preferably performed at room temperature, i.e., 20° C.-30° C. Unless otherwise specified, M indicates mol/L; and the solutions mentioned below all employ water as the solvent.

Abbreviations of some chemical reagents are listed as follows: dichloromethane (DCM); ethyl acetate (EA or EtOAc); petroleum ether (PE); tetrahydrofuran (THF); N,N-dimethylformamide (DMF); diisopropylethylamine (DIEA); 4-dimethylaminopyridine (DMAP); 1-ethyl-(3-dimethylaminopropyl) carbodiimide hydrochloride (EDCI); 1-hydroxybenzotriazole (HOBT); benzotriazole-N,N,N',N'-tetramethyluronium hexafluorophosphate (HBTU); and [1,1'-bis (diphenylphosphino) ferrocene] palladium dichloride (Pd(dppf)Cl$_2$).

Example 1

Preparation of N—((S)-2-amino-1-phenyl-ethyl) isoquinoline-6-carboxamide

Step (1) Synthesis of (S)—N-benzylidene-2-methyl-propane-2-sulfonamide

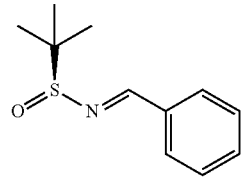

51.4 g of tert-butylsulfinamide (424 mmol) and 100 g of tetraisopropyl titanate (353 mmol) were added to a solution of 30.0 g of benzaldehyde (283 mmol) in 150 mL of tetrahydrofuran at room temperature. The reaction mixture was stirred at 60° C. for 4 h, added with water and filtered. The filtrate was extracted with ethyl acetate and separated. The aqueous phase was extracted twice with ethyl acetate. The organic phases were combined, dried with anhydrous sodium sulfate and desolventized under vacuum. The resulting product was purified by column chromatography to give 54 g of (S)—N-benzylidene-2-methylpropane-2-sulfonamide (232 mmol) with a yield of 82%.

MS (ESI) m/z=210(M+1)$^+$.

Step (2) Preparation of (S)-2-methyl-N-(2-nitro-1-phenethyl)-propane-2-sulfinamide

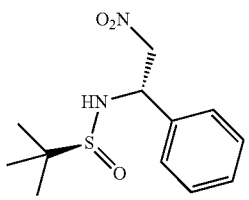 [SMILES: CC(C)(C)[S@](=O)N[C@H](C[N+](=O)[O-])c1ccccc1]

48.0 g of (S)—N-benzylidene-2-methylpropane-2-sulfonamide (229 mmol) was dissolved in 500 mL of tetrahydrofuran. The reaction mixture was added with 38.5 g of potassium tert-butoxide (344 mmol) at 0° C. under nitrogen protection and stirred for 1 h. Then the reaction mixture was added with 140 g of nitromethane (2.29 mol), stirred at room temperature for 24 h and extracted with ethyl acetate and water. The aqueous phase was extracted twice with ethyl acetate. The organic phases were combined, dried with anhydrous sodium sulfate and desolventized under vacuum.

The resulting product was purified by column chromatography to give 18 g of (S)-2-methyl-N-(2-nitro-1-phenethyl)-propane-2-sulfinamide (66.6 mmol) with a yield of 29%.

MS (ESI) m/z=271 (M+1)⁺.

Step (3) Preparation of (S)-2-methyl-N-(2-amino-1-phenethyl)-propane-2-sulfinamide

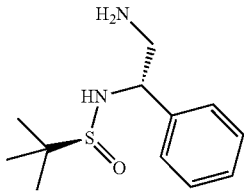 [SMILES: CC(C)(C)[S@](=O)N[C@H](CN)c1ccccc1]

8.00 g of (S)-2-methyl-N-(2-nitro-1-phenethyl)-propane-2-sulfinamide (29.6 mmol) was dissolved in 50.0 mL of methanol. The reaction mixture was added with 800 mg of Raney nickel (10%) and stirred at room temperature for 24 h. Then the reaction mixture was filtered with diatomite, and the resulting filtrate was desolventized under vacuum to give 6.00 g of (S)-2-methyl-N-(2-amino-1-phenethyl)-propane-2-sulfinamide (21.5 mmol) with a yield of 86%.

MS (ESI) m/z=241 (M+1)⁺.

Step (4) Preparation of benzyl-N—(((S)-tert-butylsulfinamide)-2-phenethyl)carbamate

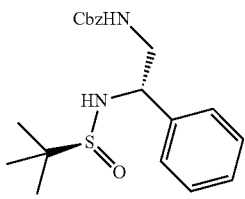 [SMILES: CC(C)(C)[S@](=O)N[C@H](CNC(=O)OCc1ccccc1)c1ccccc1]

7.00 g of (S)-2-methyl-N-(2-amino-1-phenethyl)-propane-2-sulfinamide (29.1 mmol) was dissolved in 70.0 mL of THF, to which 11.8 g of triethylamine (116 mmol) and 8.70 g of N-(benzyloxycarbonyloxy) succinimide (34.9 mmol) were added. The reaction mixture was stirred for 1 h and extracted with ethyl acetate and water. The aqueous phase was then extracted twice with ethyl acetate. The organic phases were combined, dried with anhydrous sodium sulfate and desolventized under vacuum. The resulting product was purified by column chromatography to give 6.02 g of benzyl-N—(((S)-tert-butylsulfinamide)-2-phenethyl) carbamate (12.8 mmol) with a yield of 44%.

MS (ESI) m/z=375 (M+1)⁺.

Step (5) Preparation of benzyl-N-(2-amino-2-phenyl-ethyl) carbamate

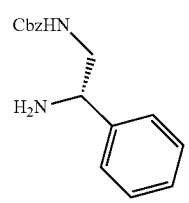 [SMILES: N[C@H](CNC(=O)OCc1ccccc1)c1ccccc1]

5.00 g of benzyl-N—(((S)-tert-butylsulfinamide)-2-phenethyl) carbamate (13.4 mmol) was dissolved in 10.0 ml of methanol, to which 40.0 mL of a solution of 5 mol/L 1,4-dioxane in hydrochloric acid was added. The reaction mixture was stirred for 1 h and desolventized under vacuum to give 3.01 g of benzyl-N-(2-amino-2-phenyl-ethyl) carbamate (10.2 mmol) with a yield of 76%.

MS (ESI) m/z=271 (M+1)⁺.

Step (6) Preparation of benzyl-N-((2S)-2-(isoquinoline-6-carboxamide)-2-phenyl-ethyl)carbamate

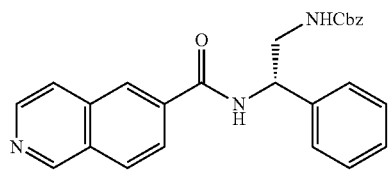 [SMILES: O=C(NC[C@@H](NC(=O)c1ccc2cnccc2c1)c1ccccc1)OCc1ccccc1]

2.00 g of benzyl-N-(2-amino-2-phenethyl) carbamate (7.40 mmol) was dissolved in 10.0 mL of DMF, to which 2.07 g of HBTU (8.14 mmol), 1.28 g of 6-isoquinolinecarboxylic acid (7.40 mmol) and 3.38 g of N,N-diisopropylethylamine (29.6 mmol) were added. The reaction mixture was stirred for 1 h and extracted with ethyl acetate and water. Then the aqueous phase was extracted twice with ethyl, and the organic phases were combined, dried with anhydrous sodium sulfate and desolventized under vacuum. The resulting product was purified by column chromatography to give 2.01 g of benzyl-N-((2S)-2-(isoquinoline-6-carboxamide)-2-phenyl-ethyl) carbamate (4.24 mmol) with a yield of 57%.

MS (ESI) m/z=426 (M-+1)⁺.

Step (7) Preparation of N—((S)-2-amino-1-phenyl-ethyl)isoquinoline-6-carboxamide

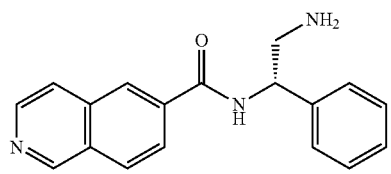 [SMILES: NC[C@@H](NC(=O)c1ccc2cnccc2c1)c1ccccc1]

300 mg of benzyl-N-((2S)-2-(isoquinoline-6-carboxamide)-2-phenyl-ethyl) carbamate was dissolved in 5.00 mL of acetic acid, to which 2.50 mL of a solution of 33% hydrobromic acid in acetic acid was added. The reaction mixture was stirred for 1 h and desolventized under vacuum to give 180 mg of N—((S)-2-amino-1-phenyl-ethyl) isoquinoline-6-carboxamide (540 µmol) with a yield of 76%.

MS (ESI) m/z=292 (M+1)⁺.

¹H NMR (400 MHz, DMSO-d₆): δ=9.78-9.84 (m 2H), 8.94 (s, 1H), 8.73-8.74 (d, J=4, 1H), 8.52-8.54 (d, J=8 Hz, 1H), 8.39-8.46 (m, 4H), 7.50-7.52 (d, J=8, 2H), 7.32-7.42 (m, 3H), 5.41-5.46 (m, 1H), 3.44-3.49 (m, 1H), 3.17-3.24 (m, 1H).

Example 2

Preparation of (S)—N-(2-amino-1-(3-bromophenyl)ethyl)isoquinoline-6-carboxamide

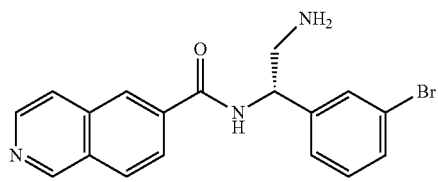 [SMILES: NC[C@@H](NC(=O)c1ccc2cnccc2c1)c1cccc(Br)c1]

(S)—N-(2-amino-1-(3-bromophenyl) ethyl) isoquinoline-6-carboxamide was prepared substantially according to steps 1-7 in Example 1, and only the benzaldehyde in step (1) was replaced with 3-bromobenzaldehyde.

MS (ESI) m/z=370, 372 (M+1)$^+$.

$^1$HNMR (400 MHz, MeOD): δ=9.91 (s, 1H), 8.96 (s, 1H), 8.65-8.71 (m, 3H), 8.49-8.52 (J=12 Hz, 1H), 7.78 (t, J=7.2 Hz, 1H), 7.54-7.57 (m, 2H), 7.36-7.42 (m, 1H), 3.64-3.75 (m, 1H), 1.87-1.81 (m, 2H).

Example 3

Preparation of (S)—N-(2-amino-1-(4-(hydroxymethyl)phenyl)ethyl)isoquinoline-6-formamide

Step (1) Preparation of isopropyl (S)-4-(((tert-butylsulfinyl)imide)methyl)benzoate

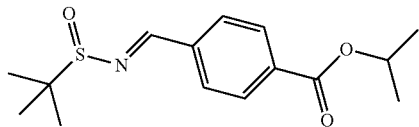 [SMILES: CC(C)OC(=O)c1ccc(/C=N/S(=O)C(C)(C)C)cc1]

To a solution of 83.1 g of (S)-tert-butylsulfinamide (685 mmol) in 50 mL of THF at room temperature was added 50.0 g of methyl 4-formylbenzoate (305 mmol) and 108 g of tetraisopropyl titanate (381 mmol). The reaction mixture was refluxed under stirring for 2 h. Then the reaction mixture was cooled, quenched with 200 mL of water and filtered to remove a white solid. The filtrate was allowed to layer, and the aqueous phase was extracted once with 200 mL of ethyl acetate. The organic phases were combined, sequentially washed with saturated brine (300 mL×1) and water (300 mL×1), dried with anhydrous Na$_2$SO$_4$ and filtered. The filtrate was desolventized under vacuum and purified by column chromatography to give 60 g of isopropyl (S, E)-4-(((tert-butylsulfinyl) imide) methyl) benzoate (203 mmol) with a yield of 67%.

MS (ESI) m/z=296 (M+1)$^+$.

Step (2) Preparation of isopropyl 4-((S)-1-((S)-1,1-dimethylethylsulfinamide)-2-nitroethyl)benzoate

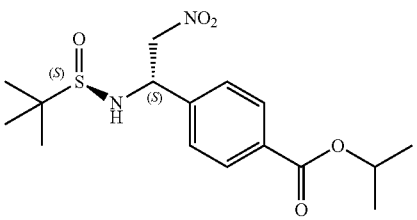

To a solution of 31.0 g of nitromethane (654 mmol) in 400 mL of THF under ice bath was batchwise added 11.0 g of potassium tert-butoxide (98.1 mmol). The reaction mixture was stirred at room temperature under nitrogen protection for 30 min and dropwise added with a solution of 18.0 g of (S)-4-(((tert-butylsulfinyl) imide) methyl) benzoate (65.4 mmol) in 200 mL of THF under ice bath. Then the reaction mixture was stirred at room temperature under nitrogen protection overnight, quenched with 400 mL of water and extracted with ethyl acetate (400 mL). The organic phase was washed once with 400 mL of saturated brine, dried with anhydrous Na$_2$SO$_4$ and filtered. The filtrate was desolventized under vacuum and purified by column chromatography to give 12 g of isopropyl 4-((S)-1-((S)-1,1-dimethylethylsulfinamide)-2-nitroethyl) benzoate (35.7 mmol) with a yield of 55%.

MS (ESI) m/z=357 (M+1)$^+$.

Step (3) Preparation of isopropyl 4-((S)-2-amino-1-((S)-1-dimethylethylsulfinamide)ethyl)benzoate

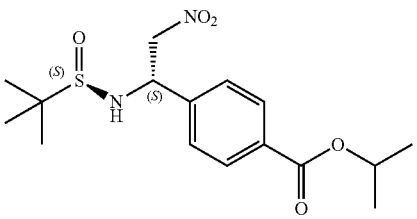

To a solution of 10.0 g of isopropyl 4-((S)-1-((S)-1,1-dimethylethylsulfinamide)-2-nitroethyl) benzoate (28.1 mmol) in 30.0 mL of methanol at room temperature under nitrogen protection was added 1.00 g of Raney nickel (10% w/w) and 1.42 g of triethylamine (14.0 mmol). The reaction mixture was stirred at room temperature under hydrogen for 4 h and filtered. The filter cake was washed with methanol, and the filtrate was desolventized under vacuum to give 9.40 g of isopropyl 4-((S)-2-amino-1-((S)-1,1-dimethylethylsulfinamide) ethyl) benzoate (26.9 mmol) with a yield of 96%.

MS (ESI) m/z=327 (M+1)$^+$.

Step (4) Preparation of (S)—N—((S)-2-amino-1-(4-(hydroxymethyl)phenyl)ethyl)-2-methylpropane-2-sulfinamide

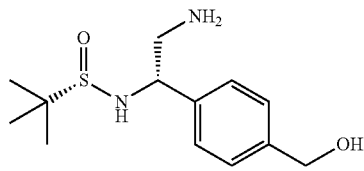 [SMILES: CC(C)(C)[S@](=O)N[C@H](CN)c1ccc(CO)cc1]

To a solution of 8.00 g of isopropyl 4-((S)-2-amino-1-((S)-1,1-dimethylethylsulfinamide) ethyl) benzoate (24.5 mmol) in 200 mL of THF at room temperature under nitrogen protection was added 4.50 g of $LiBH_4$ (204 mmol). The reaction mixture was refluxed under nitrogen for 16 h, quenched with 300 mL of water under ice bath and extracted twice with EtOAc each for 300 mL. The organic phases were combined, dried with anhydrous $Na_2SO_4$ and filtered. The filtrate was desolventized under vacuum to give 4.6 g of (S)—N—((S)-2-amino-1-(4-(hydroxymethyl) phenyl) ethyl)-2-methylpropane-2-sulfinamide (15.7 mmol) with a yield of 77%.

MS (ESI) m/z=271 $(M+1)^+$.

Step (5) Preparation of (9H-fluoren-9-yl)methyl-((S)-2-((S)-1,1-dimethylethylsulfinamide)-2-(4-(hydroxymethyl)phenyl)ethyl)carbamate

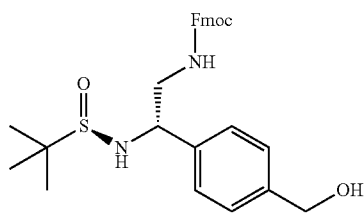

To a solution of 3.97 g of (S)—N—((S)-2-amino-1-(4-(hydroxymethyl) phenyl) ethyl)-2-methylpropane-2-sulfinamide (14.7 mmol) in a mixed solvent of 20 mL of THF and 20 mL of water at room temperature was added 7.44 g of (9H-fluoren-9-yl) methyl-(2,5-pyrrolidinedione-1-yl) carbonate (22.1 mmol) and 3.70 g of $NaHCO_3$ (44.1 mmol). The reaction mixture was stirred at room temperature for 1 h and extracted twice with ethyl acetate each for 50 mL. The organic phases were combined, washed once with 50 mL of saturated brine, dried with anhydrous $Na_2SO_4$ and filtered. The filtrate was desolventized under vacuum to give 5.00 g of (9H-fluoren-9-yl) methyl-((S)-2-((S)-1,1-dimethylethylsulfinamide)-2-(4-(hydroxymethyl) phenyl) ethyl) carbamate (9.70 mmol) with a yield of 66%.

MS (ESI) m/z=493 $(M+1)^+$.

Step (6) Preparation of (S)-(9H-fluoren-9-yl)methyl (2-amino-2-(4-(hydroxyl)phenyl)ethyl)carbamate hydrochloride

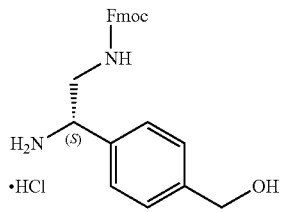

To a solution of 2.30 g of (9H-fluoren-9-yl) methyl-((S)-2-((S)-1,1-dimethylethylsulfinamide)-2-(4-(hydroxymethyl) phenyl) ethyl) carbamate (4.67 mmol) in 30 mL of methanol at room temperature was added 30 mL of a saturated dioxane hydrochloride solution. The reaction mixture was stirred at room temperature for 30 min and desolventized under vacuum to give 1.90 g of (S)-(9H-fluoren-9-yl) methyl (2-amino-2-(4-(hydroxyl) phenyl) ethyl) carbamate hydrochloride (4.47 mmol) with a yield of 96%.

MS (ESI) m/z=389 $(M+1)^+$.

Step (7) Preparation of (S)-(9H-fluoren-9-yl)methyl (2-(4-(hydroxymethyl)phenyl)-2-(isoquinoline-6-carboxamide)ethyl)carbamate

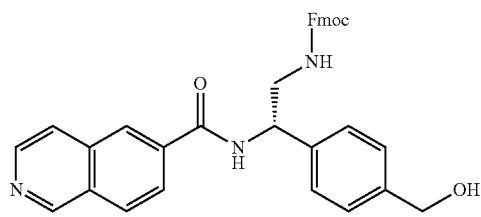

To a solution of 293 mg of 6-isoquinolinecarboxylic acid (1.69 mmol) and 600 mg of (S)-(9H-fluoren-9-yl) methyl (2-amino-2-(4-(hydroxyl) phenyl) ethyl) carbamate hydrochloride (1.41 mmol) in 10.0 mL of DMF at room temperature was added 325 mg of EDCI (1.69 mmol), 229 mg of HOBT (1.69 mmol) and 17.2 mg of DMAP (0.14 mmol). The reaction mixture was stirred at room temperature for 2 h, quenched with 30 mL of water and extracted twice with EtOAc each for 30 mL. The organic phases were combined, washed once with 30 mL of saturated brine, dried with anhydrous $Na_2SO_4$ and filtered. The filtrate was desolventized under vacuum and purified by column chromatography to give 497 mg of (S)-(9H-fluoren-9-yl) methyl (2-(4-(hydroxymethyl) phenyl)-2-(isoquinoline-6-carboxamide) ethyl) carbamate (0.86 mmol) with a yield of 60%.

MS (ESI) m/z=544 $(M+1)^+$.

Step (8) Preparation of (S)—N-(2-amino-1-(4-(hydroxymethyl)phenyl)ethyl)isoquinoline-6-carboxamide

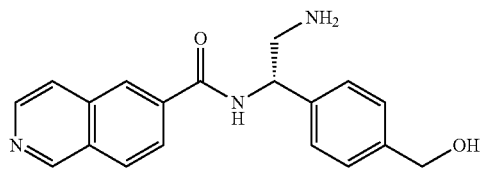 [SMILES: NC[C@@H](NC(=O)c1ccc2cnccc2c1)c1ccc(CO)cc1]

To a solution of 140 mg of (S)-(9H-fluoren-9-yl) methyl (2-(4-(hydroxymethyl) phenyl)-2-(isoquinoline-6-carboxamide) ethyl) carbamate (0.258 mmol) in 15.0 mL of THF at room temperature was added 219 mg of piperidine (2.58 mmol). The reaction mixture was stirred at room temperature for 1 h, desolventized under vacuum and purified by MPLC to give 38.4 mg of (S)—N-(2-amino-1-(4-(hydroxymethyl) phenyl) ethyl) isoquinoline-6-carboxamide (92.4 μmol) with a yield of 95%.

MS (ESI) m/z=322 (M+1)$^+$.

$^1$H NMR (400 MHz, MeOD): δ=9.91 (s, 1H), 8.90 (d, J=16.48 Hz, 1H), 8.71 (d, J=6.8 Hz, 1H), 8.66 (s, 1H), 8.64 (s, 1H), 8.48 (dd, J=1.52 Hz, J=1.60 Hz, 1H), 7.56 (s, 1H), 7.54 (s, 1H), 7.47 (s, 1H), 7.45 (s, 1H), 5.57 (q, 1H), 4.67 (q. 2H), 3.62 (t, 1H), 3.49 (t, 1H).

Example 4

Preparation of (S)-4-(2-amino-1-(isoquinoline-6-formamido)ethyl)benzyl 2,4-dimethylbenzoate Step (1) Preparation of (S)-4-(2-((((9H-fluoren-9-yl)methoxy)carbonyl)amino)-1-(isoquinoline-6-formamido)ethyl)benzyl 2,4-dimethylbenzoate

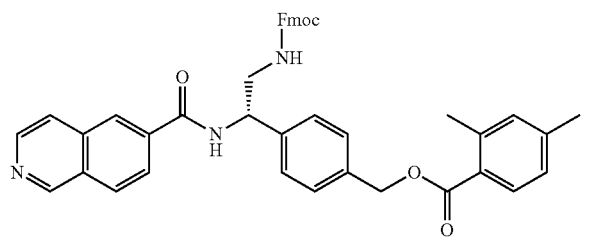

To a solution of 158 mg of (S)-(9H-fluoren-9-yl) methyl (2-(4-(hydroxymethyl) phenyl)-2-(isoquinoline-6-formamide) ethyl) carbamate (281 μmol) and 50.7 mg of 2,4-dimethylbenzoic acid (328 μmol) in 40.0 mL of dichloromethane at room temperature was added 70.2 mg of EDCI (366 μmol) and 3.44 mg of DMAP (128 μmol). The reaction mixture was stirred at room temperature overnight, desolventized under vacuum and purified by column chromatography to give 151 mg of (S)-4-(2-((((9H-fluoren-9-yl)methoxy) carbonyl) amino)-1-(isoquinoline-6-formamido) ethyl) benzyl 2,4-dimethylbenzoate (0.22 mmol) with a yield of 77%.

MS (ESI) m/z=676 (M+1)$^+$.

Step (2) Preparation of (S)-4-(2-amino-1-(isoquinoline-6-formamido)ethyl)benzyl 2,4-dimethylbenzoate

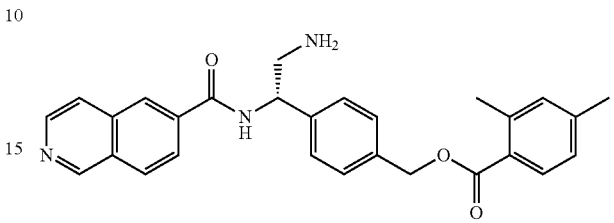

To a solution of 150 mg of (S)-4-(2-((((9H-fluoren-9-yl) methoxy) carbonyl) amino)-1-(isoquinoline-6-formamido) ethyl) benzyl 2,4-dimethylbenzoate (222 μmol) in 10.0 mL of THF at room temperature was added 378 mg of piperidine (4.44 mmol). The reaction mixture was stirred at room temperature overnight, desolventized under vacuum and purified by MPLC to give 35 mg of (S)-4-(2-amino-1-(isoquinoline-6-formamido) ethyl) benzyl 2,4-dimethylbenzoate (71.4 μmol) with a yield of 14%.

MS (ESI) m/z=454 (M+1)$^+$.

$^1$H NMR (400 MHz, MeOD): δ=9.89 (s, 1H), 8.88 (s, 1H), 8.70 (d, J=6.52 Hz, 1H), 8.65 (d, J=3.24 Hz, 1H), 8.63 (s, 1H), 8.48 (dd, J=1.48 Hz, J=1.52 Hz, 1H), 7.83 (d, J=7.96 Hz, 1H), 7.59 (q, 4H), 7.12 (s, 1H), 7.09 (d, J=8.0 Hz, 1H), 5.59 (q, 1H), 5.36 (s, 2H), 3.63 (q, 1H), 3.50 (dd, J=4.92 Hz, J=4.52 Hz, 1H), 2.55 (s, 3H), 2.36 (s, 3H).

Example 5

Preparation of N-((1S)-2-(dimethylamino)-1-phenylethyl)isoquinoline-6-formamide

Step (1) Preparation of N—((S)-2-(dimethylamino)-1-phenyl-ethyl)-2-methyl-propane-2-sulfinamide

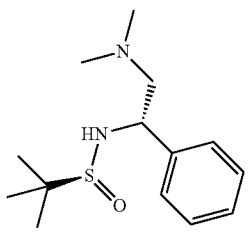 [SMILES: CN(C)C[C@@H](N[S@@](=O)C(C)(C)C)c1ccccc1]

700 mg of (S)-2-methyl-N-(2-amino-1-phenethyl)-propane-2-sulfinamide (2.96 mmol) was dissolved in 70 mL of methanol, to which 178 mg of acetic acid (2.96 mmol) and a solution of 266 mg of formaldehyde (8.88 mmol) in water were added. The reaction mixture was stirred for 1 h, added with 744 mg of sodium cyanoborohydride (11.8 mmol) and continuously reacted for 2 h. Then the reaction mixture was extracted with water and EA, and the aqueous phase was further extracted twice with EA. The organic phases were combined, dried with anhydrous sodium sulfate, desolventized under vacuum and purified by column chromatography to give 201 mg of N-((1S)-2-(dimethylamino)-1-phenyl-ethyl)-2-methyl-propane-2-sulfinamide (0.59 mmol; with a yield of 20%.

MS (ESI) m/z=269 (M+1)⁺.

Step (2) Preparation of (1S)—N',N'-dimethyl-1-phenyl-ethane-1,2-diamine

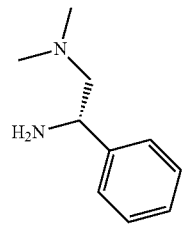

200 mg of N-((1S)-2-(dimethylamino)-1-phenyl-ethyl)-2-methyl-propane-2-sulfinamide (0.75 mmol) was dissolved in 5.0 mL of methanol, to which 10 mL of a 5 M dioxane hydrochloride acid solution was added. The reaction mixture was stirred for 1 h and desolventized under vacuum to give 100 mg of (1S)—N',N'-dimethyl-1-phenyl-ethane-1,2-diamine (0.48 mmol) with a yield of 65%.

MS (ESI) m/z=165 (M+1)⁺.

Step (3) Preparation of N-((1S)-2-(dimethylamino)-1-phenyl-ethyl)isoquinoline-6-formamide

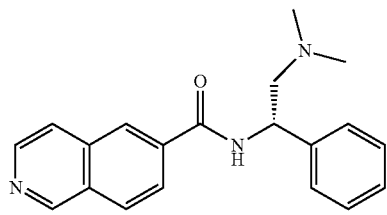 [SMILES: CN(C)C[C@@H](NC(=O)c1ccc2cnccc2c1)c1ccccc1]

90.0 mg of (1S)—N',N'-dimethyl-1-phenyl-ethane-1,2-diamine (550 μmol) was dissolved in 10.0 mL of DMF, to which 153 mg of HBTU (600 μmol), 105 mg of 6-isoquinolinecarboxylic acid (600 μmol) and 284 mg of N,N-diisopropyl ethylamine (2.19 mmol) were added. The reaction mixture was stirred for 1 h and extracted with ethyl acetate and water. Then the aqueous phase was extracted twice with ethyl acetate, and the organic phases were combined, dried with anhydrous sodium sulfate, desolventized under vacuum and purified by column chromatography to give 52 mg of N-((1S)-2-(dimethylamino)-1-phenyl-ethyl) isoquinoline-6-formamide (0.13 mmol) with a yield of 24%.

MS (ESI) m/z=320 (M+1)⁺.

¹H NMR (400 MHz, DMSO-d₆): δ=10.11 (s, 1H), 10.00-10.3 (d, J=8.4, 1H), 9.88 (s, 1H), 9.02 (s, 1H), 8.74-8.75 (d, J=6.4, 1H), 8.46-8.56 (m, 3H), 7.59-7.61 (m, 2H), 7.34-7.43 (m, 3H), 5.62-5.66 (m, 1H), 3.86-3.92 (m, 1H), 3.45-3.49 (m, 1H), 2.88-2.92 (m, 6H).

Example 6

Preparation of N-(3-amino-1-(3-chlorophenyl)propyl)isoquinoline-6-carboxamide

Step (1) Preparation of 3-amino-3-(3-chlorophenyl)acrylonitrile

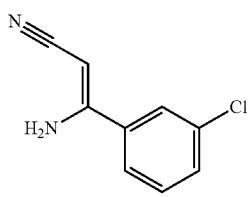 [SMILES: N#C/C=C(\N)c1cccc(Cl)c1]

To a solution of 8.00 g of chlorobenzonitrile (58.2 mmol) in 50 mL of toluene at room temperature was added 4.77 g of acetonitrile (116 mmol) and 15.0 g of potassium tert-butoxide (134 mmol). The reaction mixture was stirred for 6 h and extracted with ethyl acetate and water. The aqueous phase was further extracted twice with ethyl acetate, and the organic phases were combined, dried with anhydrous sodium sulfate, desolventized under vacuum and purified by column chromatography to give 4.99 g of 3-amino-3-(3-chlorophenyl) acrylonitrile (28.0 mmol) with a yield of 48%.

Step (2) Preparation of 3-amino-3-(3-chlorophenyl)propionitrile

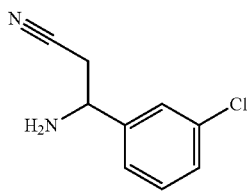 [SMILES: N#CCC(N)c1cccc(Cl)c1]

5.00 g of 3-amino-3-(3-chlorophenyl) acrylonitrile (28.0 mmol) was dissolved in 10.0 mL of ethanol, to which 2.11 g of sodium cyanoborohydride (33.6 mmol) and 1 drop of 0.5% bromocresol green ethanol solution were added at room temperature. Then concentrated hydrochloric acid was added until the reaction mixture remained yellow. The reaction mixture was continuously stirred at room temperature for 3 h, evaporated under vacuum and extracted with ethyl acetate and water. The aqueous phase was further extracted twice with ethyl acetate, and the organic phases were combined, dried with anhydrous sodium sulfate, desolventized under vacuum and purified by column chromatography to give 5.02 g of 3-amino-3-(3-chlorophenyl) propionitrile (27.7 mmol) with a yield of 99%.

MS (ESI) m/z=181 (M+1)⁺.

Step (3) Preparation of N-(1-(3-chlorophenyl)-2-cyanoethyl)isoquinoline-6-carboxamide

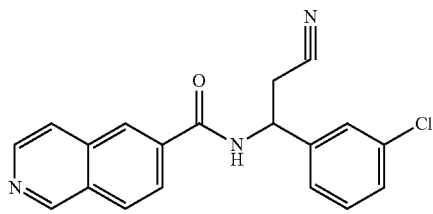 [SMILES: N#CCC(NC(=O)c1ccc2cnccc2c1)c1cccc(Cl)c1]

1.50 g of 6-isoquinolinecarboxylic acid (8.30 mmol) was dissolved in 15.0 mL of DMF, to which 3.47 g of HBTU (9.13 mmol), 3.21 g of DIEA (24.9 mmol) and 1.58 g of 3-amino-3-(3-chlorophenyl) propionitrile (9.13 mmol) were added at room temperature. The reaction mixture was stirred at room temperature for 3 h, evaporated under vacuum and extracted with ethyl acetate and water. The aqueous phase was further extracted twice with ethyl acetate, and the organic phases were combined, dried with anhydrous sodium sulfate, desolventized under vacuum and purified by column chromatography to give 1.8 g of N-(1-(3-chlorophenyl)-2-cyanoethyl) isoquinoline-6-carboxamide (5.36 mmol) with a yield of 65%.

MS (ESI) m/z=336 (M+1)$^+$.

Step (4) Preparation of N-(3-amino-1-(3-chlorophenyl) propyl) isoquinoline-6-carboxamide

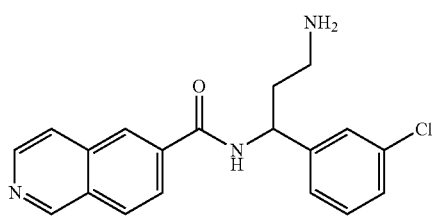 [SMILES: NCCC(NC(=O)c1ccc2cnccc2c1)c1cccc(Cl)c1]

70.0 mg of N-(1-(3-chlorophenyl)-2-cyanoethyl) isoquinoline-6-carboxamide (210 μmol) was dissolved in 5.00 mL of methanol, to which 10.0 mg of Raney nickel was added at room temperature. The reaction mixture was stirred at room temperature under hydrogen for 3 h and filtered to remove the solid. The filtrate was desolventized under vacuum and purified by MPLC to give 15.2 mg of N-(3-amino-1-(3-chlorophenyl) propyl) isoquinoline-6-carboxamide (42.0 μmol) with a yield of 20%.

MS (ESI) m/z=340 (M+1)$^+$.

$^1$H NMR (400 MHz, MeOD): δ=9.34 (s, 1H), 8.56-8.54 (m, 1H), 8.44 (s, 1H), 8.25-8.23 (m, 8.10-8.08 (m, 1H), 7.98-7.96 (m, 1H), 7.53-7.52 (m, 1H), 7.44-7.41 (m, 1H), 7.39-7.37 (m, 1H), 7.34-7.31 (m, 1H) 5.31-5.27 (m, 1H), 2.92-2.78 (m, 2H), 2.24-2.06 (m. 2H).

Example 7

Preparation of ethyl 4-(3-(3-amino-1-(isoquinoline-6-formamide)propyl)phenyl)thiophene-2-carboxylate Step (1) Preparation of tert-butyl(1-(3-chlorophenyl)-2-cyanoethyl)carbamate

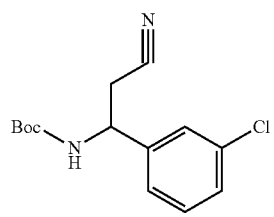 [SMILES: CC(C)(C)OC(=O)NC(CC#N)c1cccc(Cl)c1]

5.00 g of 3-amino-3-(3-chlorophenyl) propionitrile (27.7 mmol) was dissolved in 100 mL of a mixed solvent of THF. H$_2$O and MeOH (in a volume ratio of 4:1:1), to which 8.80 g of sodium carbonate (83.0 mmol) and 6.65 g of di-tert-butyl carbonate (30.5 mmol) were added at room temperature. The reaction mixture was stirred at room temperature for 3 h, desolventized under vacuum and extracted with ethyl acetate and water. The aqueous phase was extracted twice with ethyl acetate, and the organic phases were combined, dried with anhydrous sodium sulfate, desolventized under vacuum and purified by column chromatography to give 5.6 g of tert-butyl (1-(3-chlorophenyl)-2-cyanoethyl) carbamate (20 mmol) with a yield of 72%.

MS (ESI) m/z=281 (M+1)$^+$.

Step (2) Preparation of tert-butyl (3-amino-1-(3-chlorophenyl)propyl)carbamate

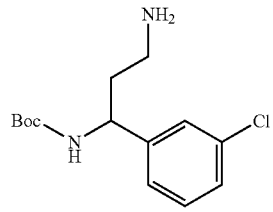 [SMILES: CC(C)(C)OC(=O)NC(CCN)c1cccc(Cl)c1]

2.00 g of tert-butyl (1-(3-chlorophenyl)-2-cyanoethyl) carbamate (7.12 mmol) was dissolved in 25.0 mL of methanol, to which 200 mg of Raney nickel was added at room temperature. The reaction mixture was stirred at room temperature under hydrogen for 3 h and filtered to remove the solid. The filtrate was desolventized under vacuum and purified by MPLC to give 2.01 g of tert-butyl (3-amino-1-(3-chlorophenyl) propyl) carbamate (7.02 mmol) with a yield of 99%.

MS (ESI) m/z=285 (M+1)$^+$.

Step (3) Preparation of benzyl tert-butyl (1-(3-chlorophenyl)propane-1,3-substituted)dicarbamate

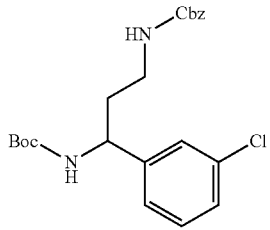 [SMILES: CC(C)(C)OC(=O)NC(CCNC(=O)OCc1ccccc1)c1cccc(Cl)c1]

2.00 g of tert-butyl (3-amino-1-(3-chlorophenyl) propyl) carbamate (7.02 mmol) was dissolved in 50.0 mL of THF, is which 2.13 g of triethylamine (21.1 mmol) was added at room temperature. The reaction mixture was stirred at room temperature for 3 h, desolventized under vacuum and extracted with ethyl acetate and water. Then the aqueous phase was further extracted twice with ethyl acetate, and the organic phases were combined, dried with anhydrous sodium sulfate, desolventized under vacuum and purified by column chromatography to give 2.81 g of benzyl tert-butyl (1-(3-chlorophenyl) propane-1,3-substituted) dicarbamate (6.68 mmol) with a yield of 95%.

Step (4) Preparation of benzyl tert-butyl (1-(3-(4,4,5,5-tetramethyl-1,3,2-dioxaborolan-2-yl)phenyl)propane-1,3-substituted)dicarbamate

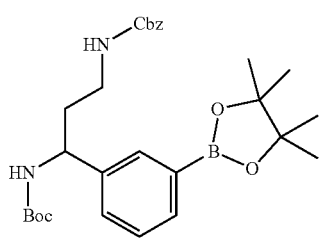 [SMILES: CC(C)(C)OC(=O)NC(CCNC(=O)OCc1ccccc1)c1cccc(B2OC(C)(C)C(C)(C)O2)c1]

2.20 g of benzyl tert-butyl (1-(3-chlorophenyl) propane-1,3-substituted) dicarbamate (5.25 mmol) was dissolved in 30.0 mL of 1,4-dioxane, to which 5.34 g of bis (pinacolato) diboron (421 mmol), 43.1 mg of 2-dicyclohexylphosphine-2',6'-dimethoxybiphenyl (110 µmol), 118 mg of palladium acetate (530 µmol) and 1.54 g of potassium acetate (15.8 mmol) were added at room temperature. The reaction mixture was stirred at 100° C. under nitrogen protection for 4 h, desolventized under vacuum and extracted with ethyl acetate and water. Then the aqueous phase was further extracted twice with ethyl acetate, and the organic phases were combined, dried with anhydrous sodium sulfate, desolventized under vacuum and purified by column chromatography to give 1.5 g of benzyl tert-butyl (1-(3-(4,4,5,5-tetramethyl-1,3,2-dioxaborolan-2-yl) phenyl) propane-1,3-substituted) dicarbamate (2.94 mmol) with a yield of 56%.

MS (ESI) m/z=511 (M+1)$^+$.

Step (5) Preparation of ethyl 4-(3-(3-(benzyloxyformamide)-1-(tert-butoxycarbonylamide)propyl)phenyl)thiophene-2-carboxylate

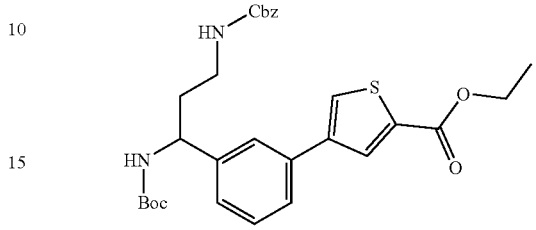

1.20 g of benzyl tert-butyl (1-(3-(4,4,5,5-tetramethyl-1,3,2-dioxaborolan-2-yl) phenyl) propane-1,3-substituted) dicarbamate (2.35 mmol) was dissolved in 15.0 mL of 1,4-dioxane, to which 172 mg of Pd(dppf)Cl$_2$ (240 µmol), 975 mg of potassium carbonate (7.05 mmol) and 608 mg of 4-bromothiophene-2-carboxylate (2.59 mmol) were added at room temperature. The reaction mixture was stirred at 100° C. under nitrogen protection for 4 h, desolventized under vacuum and extracted with ethyl acetate and water. Then the aqueous phase was further extracted twice with ethyl acetate, and the organic phases were combined, dried with anhydrous sodium sulfate, desolventized under vacuum and purified by column chromatography to give 1.1 g of ethyl 4-(3-(3-(benzyloxyformamide)-1-(tert-butoxycarbonylamide) propyl) phenyl) thiophene-2-carboxylate (2.04 mmol) with a yield of 87%.

MS (ESI) m/z=539 (M+1)$^+$.

Step (6) Preparation of ethyl 4-(3-(1-amino-3-(benzyloxyformamide)propyl)phenyl)thiophene-2-carboxylate

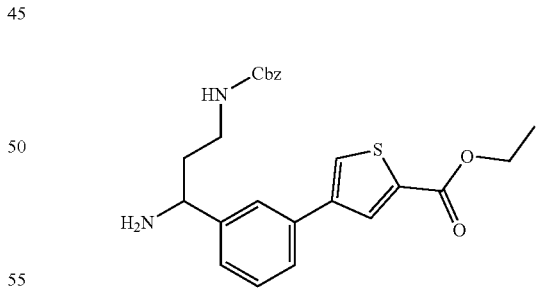

1.10 g of ethyl 4-(3-(3-(benzyloxyformamide)-1-(tert-butoxycarbonylamide) propyl) phenyl) thiophene-2-carboxylate (2.04 mmol) was dissolved in 10.0 mL of methanol, to which 5.00 mL of concentrated hydrochloric acid was added at room temperature. The reaction mixture was stirred at room temperature for 3 h, desolventized under vacuum and purified by MPLC to give 864 mg of ethyl 4-(3-(1-amino-3-(benzyloxyformamide) propyl) phenyl) thiophene-2-carboxylate (1.97 mmol) with a yield of 97%.

MS (ESI) m/z=439 (M+1)$^+$.

Step (7) Preparation of ethyl 4-(3-(3-(benzyloxyformamide)-1-(isoquinoline-6-formamide)propyl)phenyl)thiophene-2-carboxylate

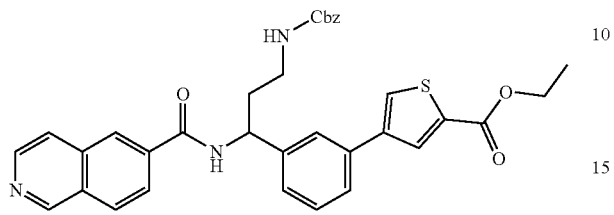

390 mg of 6-isoquinolinecarboxylic acid (2.26 mmol) was dissolved in 15.0 mL of DMF, to which 573 mg of HBTU (2.26 mmol), 794 mg of DIEA. (6.16 mmol) and 900 mg of ethyl 4-(3-(1-amino-3-(benzyloxyformamide) propyl) phenyl) thiophene-2-carboxylate were added at room temperature. The reaction mixture was stirred at room temperature for 3 h, desolventized under vacuum and extracted with ethyl acetate and water. Then the aqueous phase was further extracted twice with ethyl acetate, and the organic phases were combined, dried with anhydrous sodium sulfate, desolventized under vacuum and purified by column chromatography to give 1.01 g of ethyl 4-(3-(3-(benzyloxyformamide)-1-(isoquinoline-6-formamide) propyl) phenyl) thiophene-2-carboxylate (1.68 mmol) with a yield of 83%.

MS (ESI) m/z=594 (M+1)$^+$.

Step (8) Preparation of ethyl 4-(3-(3-amino-1-(isoquinoline-6-formamide)propyl)phenyl)thiophene-2-carboxylate

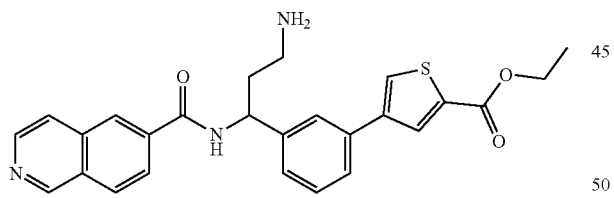

1.00 g of ethyl 4-(3-(3-(benzyloxyformamide)-1-(isoquinoline-6-formamide) propyl) phenyl) thiophene-2-carboxylate (1.68 mmol) was dissolved in 5.00 mL of acetic acid, to which 5.00 mL of a solution of hydrobromic acid in acetic acid was added at room temperature. The reaction mixture was stirred at room temperature for 3 h, desolventized under vacuum and purified by MPLC to give 50.3 mg of ethyl 4-(3-(3-amino-1-(isoquinoline-6-formamide) propyl) phenyl) thiophene-2-carboxylate (0.09 mmol) with a yield of 5.3%.

MS (ESI) m/z=594 (M+1)$^+$.

$^1$H NMR (400 MHz, MeOD): δ=9.34 (s, 1H), 8.55-8.54 (m, 2H), 8.46 (s, 1H), 8.25-8.22 (m, 1H), 8.19-8.18 (m, 1H), 8.12-8.09 (m, 1H), 8.02-8.01 (m, 1H), 7.97-7.96 (m, 1H), 7.85 (s, 1H), 7.70-7.67 (m, 1H), 7.51-7.50 (m, 2H), 5.40-5.37 (m, 1H), 4.41-4.36 (m, 2H), 3.36-3.12 (m, 1H), 3.06-2.99 (m, 1H), 2.51-2.31 (m, 2H), 1.40 (t, J=6.8 Hz, 3H).

Example 8

Preparation N-(3-(dimethylamino)-1-phenyl-propyl)isoquinoline-6-formamide

Step (1) Preparation of tert-butyl N-(3-(dimethylamino)-1-phenyl-propyl)carbamate

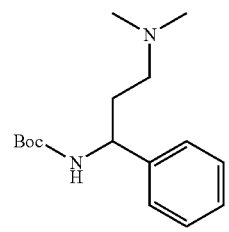

500 mg of tert-butyl (1-(3-chlorophenyl)-2-cyanoethyl) carbamate (1.78 mmol) was dissolved in 10.0 mL of methanol, to which 50.0 mg of Pd/C was added at room temperature. The reaction mixture was stirred at room temperature under hydrogen for 3 h, added with a solution of 535 mg of formaldehyde (17.8 mmol) in water and stirred at room temperature under hydrogen again for 3 h. Then the reaction mixture was filtered to remove the solid, and the filtrate was desolventized under vacuum and purified by column chromatography to give 402 mg of tert-butyl N-(3-(dimethylamino)-1-phenyl-propyl) carbamate (1.44 mmol) with yield of 81%.

MS (ESI) m/z=279 (M+1)$^+$.

Step (2) Preparation of N',N'-dimethyl-1-phenyl-propyl-1,3-diamine

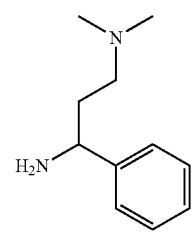

200 mg of tert-butyl N-(3-(dimethylamino)-1-phenyl-propyl) carbamate (0.72 mmol) was dissolved in 5.00 mL of methanol, to which 5.00 mL of concentrated hydrochloric acid was added at room temperature. The reaction mixture was stirred at room temperature for 3 h, desolventized under vacuum and purified by MPLC to give 121 mg of N',N'-dimethyl-1-phenyl-propyl-1,3-diamine (0.67 mmol) with a yield of 94%.

MS (ESI) m/z=179 (M+1)$^+$.

Step (3) Preparation of N-(3-(dimethylamino)-1-phenyl-propyl)isoquinoline-6-formamide

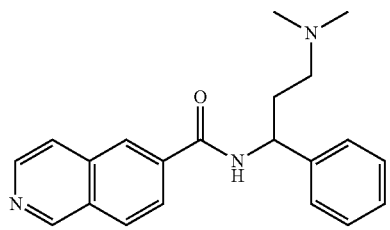 [SMILES: CN(C)CCC(NC(=O)c1ccc2cnccc2c1)c1ccccc1]

100 mg of 6-isoquinolinecarboxylic acid (570 μmol) was dissolved in 5.00 mL of DMF, to which 219 mg of HBTU (570 μmol), 224 mg of DIEA (1.73 mmol) and 100 mg of N',N'-dimethyl-1-phenyl-propyl-1,3-diamine (570 μmol) were added at room temperature. Then the reaction mixture was stirred at room temperature for 3 h, desolventized under vacuum and extracted with ethyl acetate and water. The aqueous phase was extracted twice with ethyl acetate, and the organic phases were combined, dried with anhydrous sodium sulfate, desolventized under vacuum and purified by column chromatography to give 39.6 mg of N-(3-(dimethylamino)-1-phenyl-propyl) isoquinoline-6-formamide (120 μmol) with a yield of 21%.

MS (ESI) m/z=334 (M+1)$^+$.

$^1$H NMR (400 MHz, MeOD): δ=9.80 (s, 1H), 8.74 (s, 1H), 8.46 (s, 1H), 8.66 (d, J=6.0 Hz, 1H), 8.58-8.54 (m, 2H), 8.37-8.35 (m, 1H), 7.56-7.53 (m, 1H), 7.46-7.43 m, 1H)), 7.38-7.34 (m, 1H), 5.34-5.31 (m, 1H), 3.48-3.36 (m, 1H), 3.29-3.19 (m, 1H), 2.96 (s, 6H), 2.56-2.46 (m, 1H), 2.44-2.35 (m, 1H).

Example 9

Preparation of (N-azetidin-yl-benzyl)isoquinoline-6-formamide

Step (1) Preparation of 1-diphenylmethyl-N-methoxy-N-methyl-azetidine-3-carboxamide

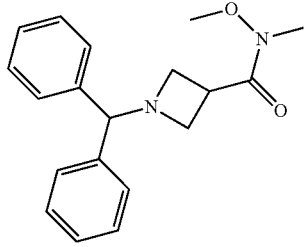 [SMILES: CON(C)C(=O)C1CN(C(c2ccccc2)c2ccccc2)C1]

To a solution of 10.0 g of 1-phenyl azetidine-3-carboxylic acid (37.4 mmol) in 100 mL of dichloromethane at room temperature was added 19.3 g of N,N-diisopropylethylamine (150 mmol), 5.56 g of N-hydroxy-7-azabenzotriazole (41.2 mmol) and 7.90 g of 1-(3-dimethylaminopropyl)-3-ethylcarbodiimide hydrochloride (41.2 mmol). The reaction mixture was stirred at room temperature for 4 h and extracted with ethyl acetate. Then the aqueous phase was extracted twice with ethyl acetate and water, and the organic phases were combined, dried with anhydrous sodium sulfate, desolventized under vacuum and purified by column chromatography to give 9.8 g of 1-diphenylmethyl-N-methoxy-N-methyl-azetidine-3-carboxamide (29.0 mmol) with a yield of 78%.

MS (ESI) m/z=311 (M+1)$^+$.

Step (2) Preparation of (1-diphenylmethyl azetidin-3-yl)-phenyl-methanone

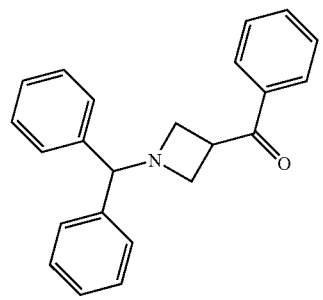 [SMILES: O=C(c1ccccc1)C1CN(C(c2ccccc2)c2ccccc2)C1]

5.00 g of 1-diphenylmethyl-N-methoxy-N-methyl-azetidine-3-carboxamide (16.1 mmol) was dissolved in 50 mL of THF, to which 80.6 mL of a 1 M phenylmagnesium bromide (80.6 mmol) solution was added under nitrogen protection at 0° C. The reaction mixture was stirred for 1 h, heated to room temperature and reacted for 1 h. Then the reaction mixture was quenched with saturated ammonium chloride solution and extracted with ethyl acetate. The aqueous phase was further extracted twice with ethyl acetate, and the organic phases were combined, dried with anhydrous sodium sulfate, desolventized under vacuum and purified by column chromatography to give 3.02 g of (1-diphenylmethyl azetidin-3-yl)-phenyl-methanone (8.25 mmol) with a yield of 51%.

MS (ESI) m/z=328 (M+1)$^+$.

Step (3) Preparation of (1-diphenylmethyl azetidin-3-yl)-phenyl-methylamine

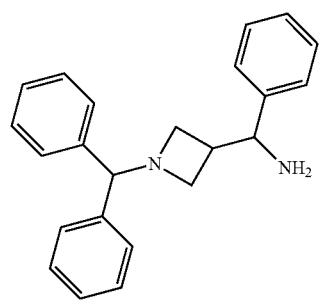 [SMILES: NC(c1ccccc1)C1CN(C(c2ccccc2)c2ccccc2)C1]

500 mg of (1-diphenylmethyl azetidin-3-yl)-phenyl-methanone (1.53 mmol) was dissolved in a mixed solvent of 25 mL of methanol and 25 mL of dichloromethane, to which 90.0 mg of acetic acid (1.53 mmol) and 1.47 g of ammonium acetate (6.11 mmol) were added. The reaction mixture was reacted under nitrogen for 1 h and added with 380 mg of sodium cyanoborohydride (6.11 mmol). Then the reaction mixture was quenched with a saturated ammonium chloride solution and extracted twice with ethyl acetate. The aqueous phase was extracted twice with ethyl acetate, and the organic phases were combined, dried with anhydrous sodium sulfate, desolventized under vacuum and purified by column chromatography to give 199 mg of (1-diphenylmethyl azetidin-3-yl)-phenyl-methylamine (0.53 mmol) with a yield of 34%.

Step (4) Preparation of tert-butyl N-((1-diphenylmethyl azetidin-3-yl)-phenyl-methyl)carbamate

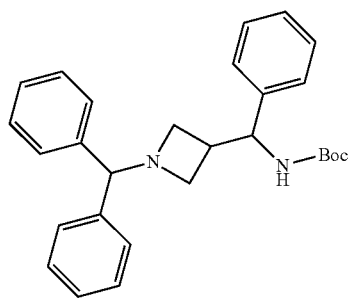 [SMILES: CC(C)(C)OC(=O)NC(c1ccccc1)C1CN(C(c2ccccc2)c2ccccc2)C1]

1.20 g of (1-diphenylmethyl azetidin-3-yl)-phenyl-methylamine (3.65 mmol) was dissolved in 70 mL of THF, to which 2.01 g of potassium carbonate (14.6 mmol) and 875 mg of di-tert-butyl dicarbonate (4.02 mmol) were added. The reaction mixture was stirred for 1 h and extracted with ethyl acetate and water. Then the aqueous phase was extracted twice with ethyl acetate, and the organic phases were combined, dried with anhydrous sodium sulfate, desolventized under vacuum and purified by column chromatography to give 1.10 g of tert-butyl N-((1-diphenylmethyl azetidin-3-yl)-phenyl-methyl) carbamate (2.31 mmol) with a yield of 63%.

Step (5) Preparation of tert-butyl N-(azetidin-3-yl-phenyl-methyl)carbamate

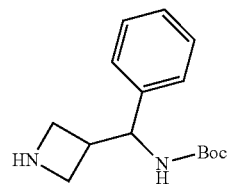 [SMILES: CC(C)(C)OC(=O)NC(c1ccccc1)C1CNC1]

1.20 g of tert-butyl N-((1-diphenylmethyl azetidin-3-yl)-phenyl-methyl) carbamate (2.80 mmol) was dissolved in 10 mL of methanol, to which 39 mg of 10% palladium hydroxide was added. The reaction mixture was stirred under hydrogen for 24 h and filtered with diatomite. The filtrate was desolventized to give 503 mg of tert-butyl N-(azetidin-3-yl-phenyl-methyl) carbamate (1.52 mmol) with a yield of 54%.

MS (ESI) m/z=263 (M+1)$^+$.

Step (6) Preparation of allyl 3-(tert-butoxycarbonylamino)-phenyl-methyl)azetidine-1-carboxylate

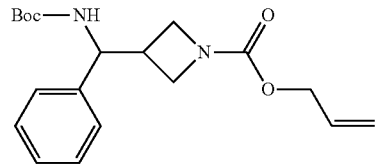 [SMILES: C=CCOC(=O)N1CC(C(NC(=O)OC(C)(C)C)c2ccccc2)C1]

1.00 g of tert-butyl N-(azetidin-3-yl-phenyl-methyl) carbamate (3.81 mmol) was dissolved in 10 mL of THF, to which 770 mg of triethylamine (7.62 mmol) and 367 mg of allyl chloroformate (3.05 mmol) were added. The reaction mixture was stirred for 2 h and extracted with ethyl acetate and water. Then the aqueous phase was extracted twice with ethyl acetate, and the organic phases were combined, dried with anhydrous sodium sulfate, desolventized under vacuum and purified by column chromatography to give 597 mg of allyl 3-((tert-butoxycarbonylamino-phenyl-methyl) azetidine-1-carboxylate (1.39 mmol) with a yield of 55%.

MS (ESI) m/z=347 (M+1)$^+$.

Step (7) Preparation of allyl 3-(amino-phenyl-methyl)azetidine-1-carboxylate

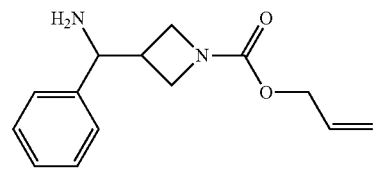 [SMILES: C=CCOC(=O)N1CC(C(N)c2ccccc2)C1]

500 mg of allyl 3-((tert-butoxycarbonylamino)-phenyl-methyl) azetidine-1-carboxylate (1.44 mmol) was dissolved in 10.0 mL of methanol, to which 3.00 mL of concentrated hydrochloride acid was added under ice bath. The reaction mixture was stirred for 2 h and desolventized to give 121 mg of allyl 3-(amino-phenyl-methyl) azetidine-1-carboxylate (0.39 mmol) with a yield of 27%.

Step (8) Preparation of allyl 3-(isoquinoline-6-formamide)benzyl)azetidine-1-carboxylate

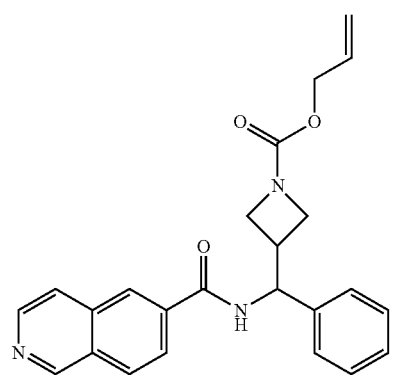 [SMILES: C=CCOC(=O)N1CC(C(NC(=O)c2ccc3cnccc3c2)c2ccccc2)C1]

To a solution of 150 mg of allyl 3-(amino-phenyl-methyl) azetidine-1-carboxylate (610 μmol) in 10.0 mL of DMF at room temperature was added 315 mg of N,N-diisopropyl ethylamine (2.44 mmol), 120 mg of N-hydroxy-7-azabenzotriazole (0.61 mmol) and 156 mg of 1-(3-dimethylaminopropyl)-3-ethylcarbodiimide hydrochloride (0.61 mmol). The reaction mixture was stirred at room temperature for 4 h and extracted with ethyl acetate. Then the aqueous phase was extracted twice with ethyl acetate and water, and the organic phases were combined, dried with anhydrous sodium sulfate, desolventized under vacuum and purified by column chromatography to give 121 mg of allyl 3-((isoquinoline-6-formamide) benzyl) azetidine-1-carboxylate (0.27 mmol) with a yield of 44%.

MS (ESI) m/z=402 (M+1)$^+$.

Step (9) Preparation of
N-(azetidin-3-yl-benzyl)isoquinoline-6-carboxamide

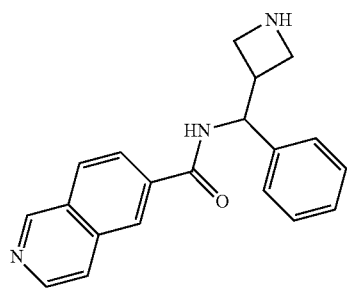 [SMILES: O=C(NC(c1ccccc1)C1CNC1)c1ccc2cnccc2c1]

To a solution of 120 mg of allyl 3-((isoquinoline-6-formamide) benzyl) azetidine-1-carboxylate (0.30 mmol) in 5.00 mL of THF at room temperature was added 3.45 mg of tetra(triphenylphosphine) palladium (0.30 mmol) and 260 mg of morpholine (2.99 mmol). The reaction mixture was stirred at room temperature for 2 h, desolventized under vacuum and purified by column chromatography to give 6.0 mg of N-(azetidin-3-yl-benzyl) isoquinoline-6-carboxamide (0.14 μmol) with a yield of 4.9%.

MS (ESI) m/z=318 (M+1)$^+$.
$^1$H NMR (400 MHz, DMSO-d$_6$+D$_2$O): δ=978 (s, 1H), 8.62-8.68 (m, 2H), 8.49-8.55 (m, 2H), 8.24-8.26 (d, J=8.8 Hz, 1H), 7.31-7.45 (m 5H), 5.39-5.41 (d, J=10.4 Hz, 1H), 4.12-4.16 (m, 1H), 3.85-3.95 (m, 2H), 3.72-3.78 (m, 1H), 3.42-3.48 (m, 1H).

Example 10

Preparation of (methyl-N-azetidine-benzyl)isoquinoline-6-carboxamide

Step (1) Preparation of t-butyl(methyl-N-azetidin-3-yl(phenyl)methyl)carbamate

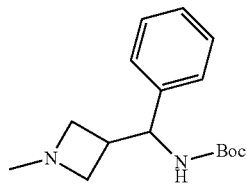 [SMILES: CN1CC(C(NC(=O)OC(C)(C)C)c2ccccc2)C1]

1.00 g of t-butyl N-(azetidin-3-yl (phenyl) methyl) carbamate (3.81 mmol) was dissolved in 10.0 mL of methanol, to which 266 mg of acetic acid (0.81 mmol) and a solution of 572 mg of formaldehyde (19.1 mmol) in water were added. The reaction mixture was stirred for 1 h, added with 239 mg of sodium cyanoborohydride (3.81 mmol), quenched with a saturated aqueous ammonium chloride solution and extracted with ethyl acetate. Then the aqueous phase was further extracted twice with ethyl acetate, and the organic phases were combined, dried with anhydrous sodium sulfate, desolventized under vacuum and purified by column chromatography to give 796 mg of t-butyl (methyl-N-azetidin-3-yl (phenyl) methyl) carbamate (2.03 mmol) with a yield of 53%.

MS (ESI) m/z=277 (M+1)$^+$.

Step (2) Preparation of
(1-methylazetidin-3-yl)-phenyl-methylamine

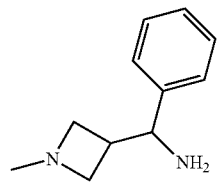

773 mg of t-butyl (methyl-N-azetidin-3-yl (phenyl) methyl) carbamate (2.80 mmol) was dissolved in 10 mL of methanol, to which 3.00 mL of concentrated hydrochloride acid was added under ice bath. The reaction mixture was stirred for 2 h and desolventized under vacuum to give 0.48 g of (1-methylazetidin-3-yl)-phenyl-methylamine (2.2 mmol) with a yield of 78%.

MS (ESI) m/z=177 (M+1)$^+$.

Step (3) Preparation of N-((1-methylazetidin-3-yl)-benzyl)isoquinoline-6-carboxamide

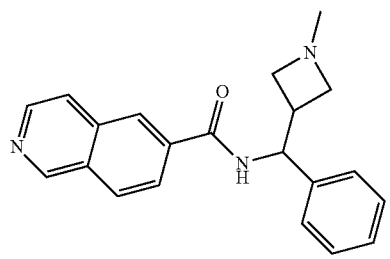 [SMILES: CN1CC(C(NC(=O)c2ccc3cnccc3c2)c2ccccc2)C1]

To a solution of 400 mg of (1-methylazetidin-3-yl)-phenyl-methylamine (2:27 mmol) in 10.0 mL of DMF at room temperature was added 1.17 g of N,N-diisopropyl ethylamine (9.08 mmol), 430 mg of N-hydroxy-7-azabenzotriazole (2.27 mmol) and 460 mg of 1-(3-dimethylaminopropyl)-3-ethylcarbodiimide hydrochloride (2.27 mmol). The reaction mixture was stirred at room temperature for 4 h and extracted with ethyl acetate. Then the aqueous phase was extracted twice with ethyl acetate and water, and the resulting organic phases were combined, dried with anhydrous sodium sulfate, desolventized under vacuum and purified by column chromatography to give 20.2 ing of N-((1-methylazetidin-3-yl)-benzyl) isoquinoline-6-carboxamide (48.0 µmol) with a yield of 2.1%.

MS (ESI) m/z=332 (M+1)+.

$^1$H NMR (400 MHz, MeOD): δ=9.86 (s, 1H), 8.77 (s, 1H), 8.60-8.68 (m, 3H), 8.36-8.38 (d, J=8.8 Hz, 1H), 7.52-7.54 (d, J=8.0 Hz, 2H), 7.42-7.45 (m, 2H), 7.36-7.38 (m, 1H), 5.51-5.60 (m, 1H), 4.44-4.58 (m, 1H), 4.11-4.23 (m, 2H), 3.96-4.02 (m, 1H), 3.62-3.71 (m, 1H), 2.96-3.01 (d, J=12 Hz, 3H).

Example 11

Preparation of N—((S)-phenyl-((R)-pyrrolidin-3-yl)methyl)isoquinoline-6-carboxamide and N—((R)-phenyl-((R)-pyrrolidin-3-yl)methyl)isoquinoline-6-carboxamide

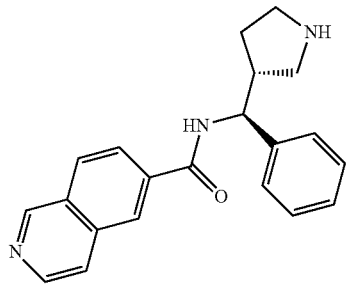

11a

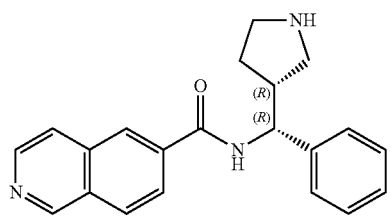

11b

Step (1) Preparation of (R)-tert-butyl 3-(methoxy (methyl)formamido)pyrrolidine-1-carboxylate

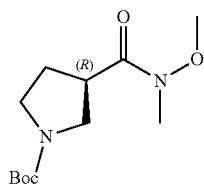

15.0 g of (R)-1-tert-butoxycarbonylpyrrolidine-3-carboxylic acid (69.7 mmol) was dissolved in 200 mL of DCM, to which 14.6 g of EDCI (76.7 mmol), 10.4 g of HOBT (76.7 mmol) 27.0 g of DIEA (209 mmol) and 6.38 g of dimethyl hydroxylamine (104.5 mmol) were added. The reaction mixture was stirred for 1 h and extracted with ethyl acetate and water. Then the aqueous phase was extracted twice with water, and the organic phases were combined, dried with anhydrous sodium sulfate, desolventized under vacuum and purified by column chromatography to give 15 g of (R)-tert-butyl 3-(methoxy (methyl) carbamoyl) pyrrolidine-1-carboxylate (58 mmol) with a yield of 83%.

MS (ESI) m/z=259 (M+1)+ and 203 (M+1−56)+.

Step (2) Preparation of tert-butyl(R)-3-benzoylpyrrolidine-1-carboxylate

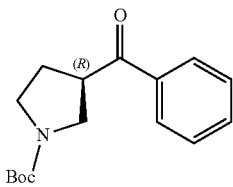

10 g of (R)-tert-butyl 3-(methoxy (methyl) carbamoyl) pyrrolidine-1-carboxylate (38.7 mmol) was dissolved in 30 mL of THF, to which 194 mL of a 1 M phenylmagnesium bromide solution (194 mmol) was dropwise added. The reaction mixture was stirred at 0° C. for 1 h and extracted with ethyl acetate and water. Then the aqueous phase was extracted twice with ethyl acetate, and the organic phases were combined, dried with anhydrous sodium sulfate, desolventized under vacuum and purified by column chromatography to give 9.1 g of tert-butyl (R)-3-benzoylpyrrolidine-1-carboxylate (33 mmol) with a yield of 84%.

MS (ESI) m/z=276 (M+1)+ and 220 (M+1−56)+.

Step (3) Preparation of tert-butyl(R)-3-((hydroxyimine)(phenyl)methyl)pyrrolidine-1-carboxylate

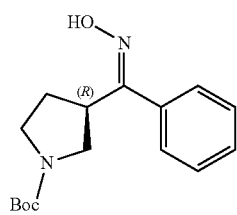

10 g of tert-butyl (R)-3-benzoylpyrrolidine-1-carboxylate (36.3 mmol) was dissolved in 150 mL of MeOH, to which 11.6 g of Na$_2$CO$_3$ (109 mmol) and 6.00 g of hydroxylamine hydrochloride (182 mmol) were added at room temperature. The reaction mixture was stirred at 50° C. for 2 h and extracted with ethyl acetate and water. Then the aqueous phase was extracted twice with ethyl acetate, and the resulting organic phases were combined, dried with anhydrous sodium sulfate, desolventized under vacuum and purified by column chromatography to give 8.1 g of tert-butyl (R)-3-((hydroxyimine) (phenyl) methyl) pyrrolidine-1-carboxylate (28 mmol) with a yield of 77%.

MS (ESI) m/z=291 (M+1) and 235 (M+1−56)+.

Step (4) Preparation of tert-butyl(R)-3-(amino(phenyl)methyl)pyrrolidine-1-carboxylate

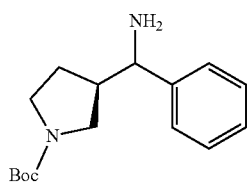 [SMILES: CC(C)(C)OC(=O)N1CC[C@@H](C(N)c2ccccc2)C1]

8.0 g of tert-butyl (R)-3-((hydroxyimine) (phenyl) methyl) pyrrolidine-1-carboxylate (27 mmol) was dissolved in 150.00 mL of MeOH, to which Raney nickel was added at room temperature. The reaction mixture was stirred at room temperature under hydrogen for 2 h and filtered under vacuum. The resulting filtrate was desolventized under vacuum and purified by column chromatography to give 4.9 g of tert-butyl (R)-3-(amino (phenyl) methyl) pyrrolidine-1-carboxylate (18 mmol) with a yield of 65%.

MS (ESI) m/z=277 (M+1)$^+$ and 221 (M+1−56)$^+$.

Step (5) Preparation of tert-butyl(R)-3-((isoquinoline-6-formamide)-phenyl-methyl)pyrrolidine-1-carboxylate

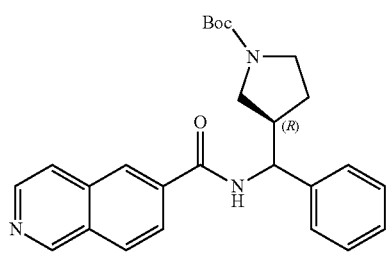

3.00 g of 6-isoquinolinecarboxylic acid (17.3 mmol) was dissolved in 20.0 mL of DMF, to which 7.26 g HBTU (19.06 mmol), 4.79 g of tert-butyl (R)-3-(amino (phenyl) methyl) pyrrolidine-1-carboxylate (17.3 mmol) and 3.38 g of diisopropyl ethylamine (29.6 mmol) were added. The reaction mixture was stirred for 1 h and extracted with ethyl acetate and water. Then the aqueous phase was extracted twice with ethyl acetate, and the organic phases were combined, dried with anhydrous sodium sulfate, desolventized under vacuum and purified by column chromatography to give 6.01 g of tert-butyl (R)-3-((isoquinoline-6-formamide)-phenyl-methyl) pyrrolidine-1-carboxylate (13.9 mmol) with a yield of 80%.

MS (ESI) m/z=432 (M+1)$^+$ and 376 (M+1−56)$^+$.

Step (6) Preparation of N—((S)-phenyl-((R)-pyrrolidin-3-yl)methyl)isoquinoline-6-carboxamide and N—((R)-phenyl-((R)-pyrrolidin-3-yl)methyl)isoquinoline-6-carboxamide

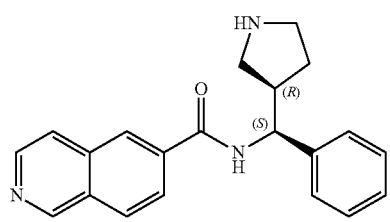
11a

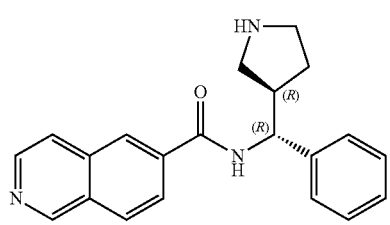
11b 5.00 g of tert-butyl (R)-3-((isoquinoline-6-formamide)-phenyl-methyl) pyrrolidine-1-carboxylate (11.6 mmol) was dissolved in 30.0 mL of ethyl acetate, to which 10.0 mL of concentrated hydrochloride acid was added. The reaction mixture was stirred for 1 h, desolventized under vacuum and treated by Pre-PLC to give 0.89 g of N—((S)-phenyl-((R)-pyrrolidin-3-yl) methyl) isoquinoline-6-carboxamide (2.69 mmol) with a yield of 23% and 1.0 g of N—((R)-phenyl-((R)-pyrrolidin-3-yl) methyl) isoquinoline-6-carboxamide (3.0 mmol) with a yield of 26%.

MS (ESI) m/z=332 (M+1)$^+$.

Compound 11a: $^1$HNMR (400 MHz, MeOD): δ=9.31 (s, 1H) 8.53-8.49 (m, 2H), 8.39 (s, 1H), 8.19 (d, J=8.8 Hz, 1H), 8.04 (d, J=8.4 Hz, 1H), 7.93 (d, J=5.6 Hz, 1H), 7.55 (d, J=7.6 Hz, 2H), 7.45-7.41 (m, 2H), 7.37-7.33 (m, 1H), 5.18 (d, J=10.0 Hz, 1H), 3.55-3.49 (m, 1H), 3.41-3.36 (m, 1H), 3.19-3.11 (m, 2H), 3.00-2.94 (m, 1H), 2.45-2.39 (m, 1H), 2.11-2.01 (m, 1H).

Compound 11b: $^1$HNMR (400 MHz, MeOD): δ=9.32 (s, 1H), 8.53 (d, J=5.6 Hz, 1H), 8.47 (s, 1H), 8.39 (s, 1H), 8.20 (d, J=8.4 Hz, 1H), 8.05 (d, J=8.8 Hz, 1H), 7.94 (d, J=6.0 Hz, 1H), 7.54 (d, J=7.6 Hz, 2H), 7.45-7.41 (m, 2H), 7.37-7.33 (m, 1H), 5.15 (d, J=10.8 Hz, 1H), 3.69-3.64 (m, 1H), 3.49-3.43 (m, 1H), 3.31-3.26 (m 2H), 3.16-3.10 (m, 1H), 1.93-1.85 (m, 1H), 1.80-1.70 (m, 1H).

Example 12

Preparation of N—((R)—((R)-1-methylpyrrolidin-3-yl)(phenyl)methyl)isoquinoline-6-carboxamide

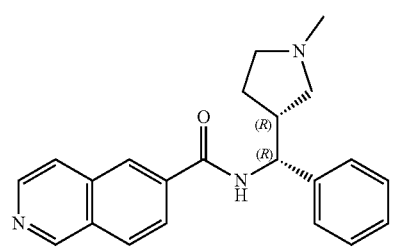

250 mg of N—((R)-phenyl-((R)-pyrrolidin-3-yl) methyl) isoquinoline-6-carboxamide (1.51 mmol) was dissolved in 15.0 mL of methanol to which 9.1 mg of acetic acid (0.15 mmol) and 0.58 mL of a 13 M aqueous formaldehyde solution (7.55 mmol) were added. The reaction mixture was stirred for 1 h, added with 0.96 g of sodium triacetoxyborohydride (4.53 mmol), reacted for 2 h and extracted with ethyl acetate and water. Then the aqueous phase was extracted twice with ethyl acetate, and the organic phases were combined, dried with anhydrous sodium sulfate, desolventized under vacuum and purified by column chromatography to give 30 mg of N—((R)—((R)-1-methylpyrrolidin-3-yl) (phenyl) methyl) isoquinoline-6-carboxamide (83 μmol) with a yield of 11%.

MS (ESI) m/z=346 (M+1)$^+$.

$^1$HNMR (400 MHz, DMSO-d$_6$): δ=11.08-10.77 (m, 1H), 9.77 (s, 1H), 9.65-9.63 (m, 1H) 8.76-8.70 (m, 2H), 8.47 (d, J=8.4 Hz, 1H), 8.37 (s, 1H), 8.27 (t, J=8.4 Hz, 1H), 7.52 (t, J=8.0 Hz, 2H), 7.41-7.36 (m, 2H), 7.32-7.28 (m, 1H), 5.16-5.07 (m, 1H), 3.82-3.77 (m, 1H), 3.55-3.48 (m, 2H), 3.30-3.15 (m, 1H), 3.13-3.05 (m, 1H), 2.81 (s, 3H), 1.79-1.61 (m, 21H).

Example 13

Preparation of N—((S)—((R)-1-methylpyrrolidin-3-yl)(phenyl)methyl)isoquinoline-6-carboxamide

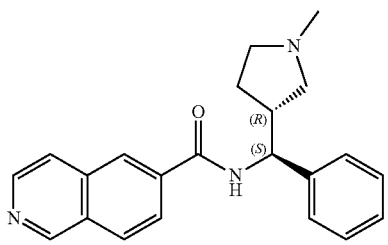

250 mg N—((S)-phenyl-((R)-pyrrolidin-3-yl) methyl) isoquinoline-6-carboxamide (1.51 mmol) was dissolved in 15.0 mL of methanol, to which 9.1 mg of acetic acid (0.15 mmol) and 0.58 mL of a 13 M aqueous formaldehyde solution (7.55 mmol) were added. The reaction mixture was stirred for 1 h, added with 0.96 g of sodium triacetoxyborohydride (4.53 mmol), reacted for 2 h and extracted with ethyl acetate and water. Then the aqueous phase was extracted twice with ethyl acetate, and the organic phases were combined, dried with anhydrous sodium sulfate, desolventized under vacuum and purified by column chromatography to give 21 mg of N—((S)—((R)-1-methylpyrrolidin-3-yl) (phenyl) methyl) isoquinoline-6-carboxamide (58 μmol) with a yield of 7.7%.

MS (ESI) m/z=346 (M+1)$^+$.

$^1$HNMR (400 MHz, DMSO-d$_6$): δ=11.17-10.90 (m, 1H), 9.79 (s, 1H), 9.65-9.48 (m, 1H), 8.81-8.70 (m, 2H), 8.49 (d, J=8.4 Hz, 1H), 8.40-8.39 (m, 1H), 8.28 (d, J=8.4 Hz, 1H), 7.57-7.49 (m, 2H), 7.41-7.37 (m, 2H), 7.32-7.29 (m, 1H), 5.19-5.10 (m, 1H), 3.63-3.51 (m, 2H), 3.25-310 (m, 2H), 3.08-2.91 (m, 1H), 2.76-2.73 (m, 3H), 2.37-2.23 (m, 1H), 2.03-1.85 (m, 1H).

Example 14

Preparation of N—((S)-phenyl-((S)-pyrrolidin-3-yl) methyl)isoquinoline-6-carboxamide and N—((R)-phenyl-((S)-pyrrolidin-3-yl)methyl)isoquinoline-6-carboxamide 14a

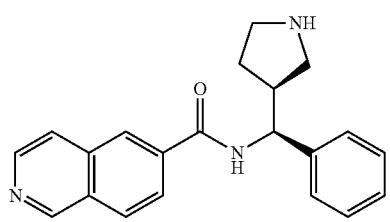

14b

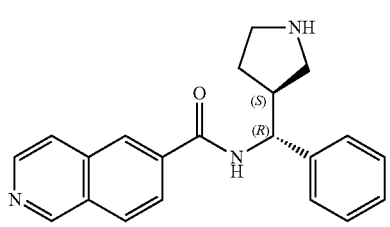

28 mg of N—((S)-phenyl-((S)pyrrolidin-3-yl) methyl) isoquinoline-6-carboxamide (5.1% yield) and 22 mg of N—((R)-phenyl-((S)-pyrrolidin-3-yl) methyl) isoquinoline-6-carboxamide (4.9% yield) were prepared herein basically according to steps 1-6 in Example 11, and the difference was only that (R)-1-tert-butoxycarbonylpyrrolidine-3-carboxylic acid in step (1) was replaced with (S)-1-tert-butoxycarbonylpyrrolidine-3-carboxylic acid.

MS (ESI) m/z=332 (M+1)$^+$.

Compound 14a: $^1$HNMR (400 MHz, DMSO-d$_6$): 9.96 (s, 1H), 9.79-9.81 (d, J=8.4 Hz, 1H), 9.51 (s, 2H), 8.8 (s, 1H), 8.75-8.76 (d, J=6 Hz, 1H), 8.57-8.61 (m, 2H), 8.37-8.40 (m, 1H), 7.58-7.59 (m, 2H), 7.36-7.40 (m, 2H), 7.30-7.31 (m, 1H), 5.09-5.14 (m, 1H), 3.29-3.31 (m, 1H), 3.36-3.18 (m, 1H), 3.2-3.06 (m, 1H), 2.83-2.89 (m, 2H), 2.23-2.27 (m, 1H), 1.82-1.88 (m, 1H).

Compound 14b: $^1$HNMR (400 MHz, DMSO-d$_6$): δ=9.90 (s, 1H), 9.84 (d, J=7.6 Hz, 1H), 9.64 (s, H), 9.50 (s, H), 8.88 (s, 1H), 8.74 (d, J=6.4 Hz, 1H), 8.49-8.57 (m, 2H), 8.35 (d, J=8.8 Hz, 1H), 7.55-7.57 (m, 2H), 7.37-7.40 (m, 2H), 7.30-7.31 (m, 1H), 5.06 (t, J=6.0 Hz, 1H), 3.5 (m, 1H), 3.28 (m, 1H), 3.06 (m, 3H), 1.64 (m, 1H).

Example 15

Preparation of N—((S)-2-(dimethylamino)-1-(3-methoxyphenyl)ethyl)isoquinoline-6-carboxamide Step (1) Preparation of N-((1S)-2-(dimethylamino)-1-(3-methoxyphenyl)ethyl)isoquinoline-6-carboxamide

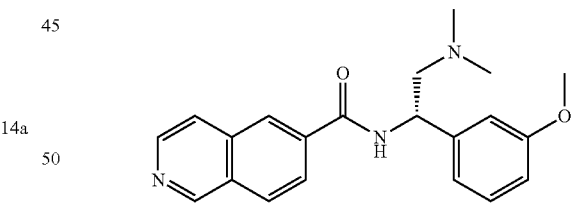

N—((S)-2-(dimethylamino)-1-(3-methoxyphenyl) ethyl) isoquinoline-6-carboxamide was prepared herein substantially according to steps 1-3 in Example 1 and steps 1-3 in Example 5, and the difference was only that the benzaldehyde in step (1) of Example 1 was replaced with 3-methoxybenzaldehyde.

MS (ESI) m/z=350 (M+1)$^+$.

$^1$HNMR (400 MHz, MeOD): δ=9.75 (s, 1H), 8.87 (s, 1H), 8.66 (d, J=6.4 Hz, 1H), 8.55-8.53 (m, 1H), 8.48 (d, J=6.4 Hz, 1H), 8.45-8.42 (m, 1H), 7.39 (t, J=8.0 Hz, 1H), 7.20-7.16 (m, 2H), 6.99-6.96 (m, 1H), 5.80-5.76 (m, 1H), 3.99-3.93 (m, 1H), 3.85 (s, 1H), 3.67-3.62 (m, 1H), 3.11-3.08 (m, 6H).

Example 16

Preparation of N—((S)-2-(dimethylamino)-1-(3-chlorophenyl)ethyl)isoquinoline-6-carboxamide Step (1) Preparation of N—((S)-2-(dimethylamino)-1-(3-chlorophenyl)ethyl)isoquinoline-6-carboxamide

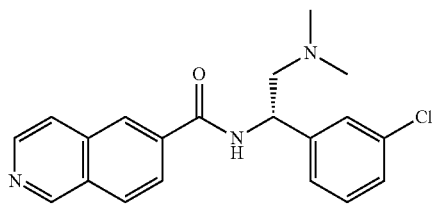 [SMILES: CN(C)C[C@@H](NC(=O)c1ccc2cnccc2c1)c1cccc(Cl)c1]

N—((S)-2-(dimethylamino)-1-(3-chlorophenyl) ethyl) isoquinoline-6-carboxamide was prepared herein substantially according to steps 1-3 in Example 1 and steps 1-3 in Example 5, and the difference was only that the benzaldehyde in step (1) of Example 1 was replaced with 3-chlorobenzaldehyde.

MS (ESI) m/z=354 (M+1)$^+$.

$^1$H NMR (400 MHz, MeOH): δ=9.91 (s, 1H), 9.06 (s, 1H), 8.72-8.64 (m, 3H), 8.57 (d, J=8.8 Hz, 2H), 7.69 (s, 1H), 7.48-7.41 (m, 2H), 5.82 (d, J=11.6 Hz, 1H), 4.06 (t, J=11.6 Hz, 1H), 3.64 (t, J=13.6 Hz, 1H), 3.12 (s, 3H), 3.08 (s, 3H).

The beneficial effects of the invention will be demonstrated below with reference to the Experimental Examples.

Experimental Example 1

Measurement of Inhibitory Activity Against ROCK2

ROCK2 was capable of phosphorylating a substrate of polypeptide S6K (KRRRLASLR) by converting ATP to ADP. An ADP-Glo™ reagent was adopted to terminate this reaction and consume the remaining ATP. Moreover, a kinase detection reagent was introduced to ensure that ATP was further converted into a luminescent signal by an Ultra-Glo™ luciferase while convening ADP into ATP, allowing the kinase activity to be positively correlated with the intensity of the luminescent signal.

The inhibitory activity against ROCK2 was determined as follows.

(1) A detection buffer containing 40 mM Tris (pH 7.5), 20 mM MgCl$_2$, 0.1% BSA(w/v) and 50 μM DTT was prepared.

(2) 12 μL of 2.5×0.1 μg/mL ROCK2 solution was added to a 96-well PCR plate.

(3) The 96-well PCR plate was added with 6 μL of a 6× compound solution and pre-incubated at 25° C. for 10 min.

(4) Then the 96-well PCR plate was further added with 12 μL of a mixed solution of a 2.5×37.5 μg/mL S6K substrate solution and a 12.5 μM ATP solution, and incubated at 30° C. for 60 min.

(5) 25 μL of the reaction mixture was transferred to a new 96-well PCR plate, mixed with 25 μL of the ADP-Glo™ reagent uniformly and incubated at 25° C. for 40 min to terminate the reaction.

(6) After the reaction was terminated, 40 μL of the reaction mixture was transferred to another 96-well PCR plate, mixed with 40 μL of the kinase detection reagent uniformly and incubated at 25° C. for 40 min.

(7) The luminescence signal was recorded for the calculation of the inhibitory rate.

The inhibitory activity of the above-prepared compounds against the ROCK2 was measured according to the above process, and the results were shown in Table 1, in which the compounds were ranked according to the IC$_{50}$ value. Specifically, "+" indicated an IC$_{50}$ value greater than 500 nM; "++" indicated an IC$_{50}$ value less than 500 nM and greater than 100 nM; and "+++" indicated an IC$_{50}$ value less than 100 nM.

TABLE 1

Inhibitory activity of the compounds against ROCK2

| Compounds | ROCK2 | Compounds | ROCK2 |
|---|---|---|---|
| 1 | +++ | 2 | +++ |
| 3 | ++ | 4 | ++ |
| 5 | +++ | 6 | +++ |
| 7 | +++ | 8 | +++ |
| 9 | +++ | 10 | +++ |
| 11a | +++ | 11b | +++ |
| 12 | +++ | 13 | +++ |
| 14a | ++ | 14b | +++ |
| 15 | +++ | | |

It can be seen from the results that the compounds prepared herein had a good enzymatically-inhibitory activity on ROCK2.

Experimental Example 2

Detection of Light Chain Phosphorylation of Myosin By In-Cell Western Blotting ROCK2 was capable of altering the cytoskeleton by phosphorylating two amino acid sites (T18 and S19) on the myosin light chain. Smooth muscle cells A7r5 of rats were selected, inoculated into a 96 well black plate with a transparent bottom and cultured with DMEM containing 10% FBS. After cultured overnight, the cells were treated by serum starvation for 4 h and then incubated with respective compounds in serum-free medium for 1 h. The phosphorylation level of the myosin light chain was detected by In-Cell Western Blotting using a phspho-MLC-T18/S19-specific antibody and a secondary detection antibody. The untreated cells were used as positive control; the cells without undergoing primary antibody incubation were used as negative control; and total intracellular protein was used as an internal reference. The results were fitted by a non-linear regression curve with varying slope using GraphPad Prism 5.01 software to determine an IC$_{50}$ value.

The detection of the inhibitory activity of the above-prepared compounds against the phosphorylation of the myosin light chain of smooth muscle cells A7r5 was performed according to the above process. The results were shown in Table 2, where the compounds were ranked according to the IC$_{50}$ value. Specifically, "+" indicated an IC$_{50}$ value greater than 1 μM; "++" indicated an IC$_{50}$ value less than 1 μM and greater than 250 nM; and "+++" indicated an IC$_{50}$ value less than 250 nM.

TABLE 2

Inhibitory activity of the compounds prepared in Examples
1-16 against rat smooth muscle cells A7r5

| Compounds | A7r5 | Compounds | A7r5 |
|---|---|---|---|
| 1 | ++ | 2 | +++ |
| 4 | + | 5 | ++ |
| 6 | +++ | 7 | ++ |
| 8 | + | 9 | ++ |
| 10 | ++ | 11a | ++ |
| 13 | ++ | 15 | ++ |
| 16 | ++ | | |

The results demonstrated that the compounds of the invention showed a good inhibitory activity against the rat smooth muscle cells A7r5. Therefore, the compounds of the invention were capable of inhibiting the change to the cytoskeleton caused by phosphorylation of two amino acid sites T18/S19 of the myosin light chain by ROCK2, having potential activity for treating related diseases.

Experimental Example 3

Animal Experiment (Normal Intraocular Pressure Model)

24 male New Zealand rabbits were averagely divided into 4 groups, and were randomly assigned to respective groups using a computer randomized algorithm involving weight. From 3 days to 3 day before the experiment, all rabbits were required to be trained to adapt to the operation of intraocular pressure (IOP) measurement, and the training was performed 3 times a day with an interval of about 3 h. The intraocular pressure was measured using a TonoVet tonometer, specifically, individual animals were fixed and the eye to be tested was placed at a position perpendicular to the TonoVet tonometer. The IOP should be measured at least 3 times in each operation until the reading became stable. The results from the last three stable measurements (±3 mmHg) were recorded and averaged to be used as the final IOP value. Respective compounds were weighed and dissolved with normal saline to the desired concentration. At the beginning of the experiment, individual compounds of the invention, reference compound K115 or negative control solvent (50 µL) were administered to the right eye of each animal, and the left eye of each animal was treated by normal saline. The IOP was measured at time points Pre (0 h), 1 h, 2 h, 4 h, 6 h, 8 h and 10 h after the administration of drugs, and the data obtained at respective time points was analyzed by student-t test. The curve of IOP over time was analyzed using the ANOVA test, where a P value of less than 0.05 will be considered to be of statistical significance and the data was expressed by mean±standard deviation.

Figure 2:
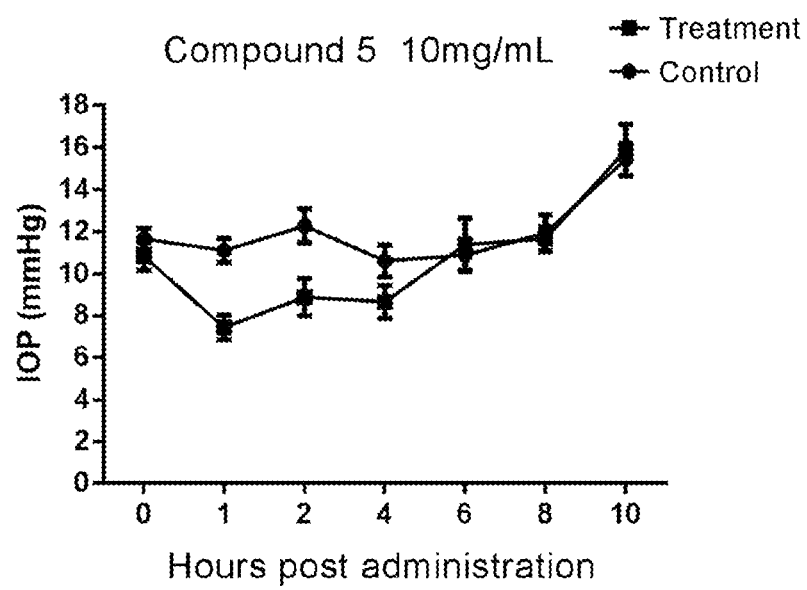
FIG. 2 shows the experimental results of the intraocular pressure-lowering activity of Compound 5 on New Zealand rabbits with normal intraocular pressure
Figure 3:
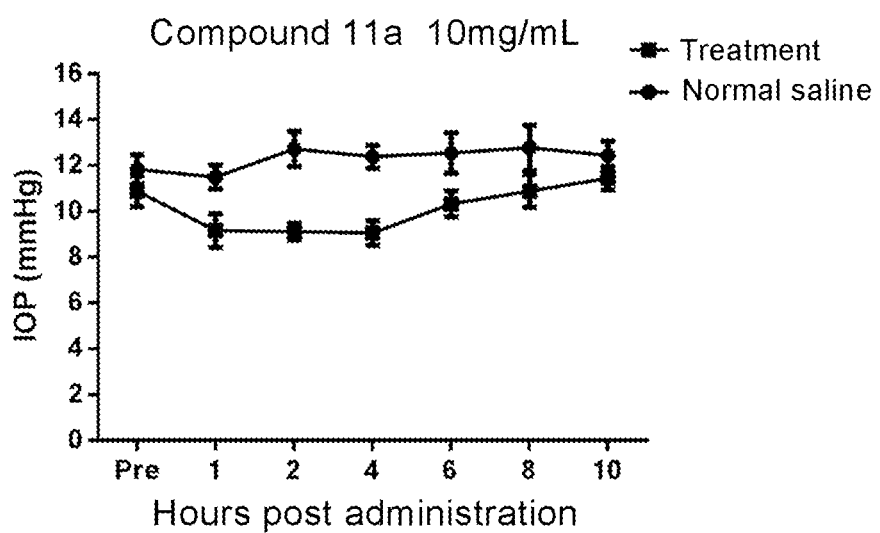
FIG. 3 shows the experimental results of the intraocular pressure-lowering activity of Compound 11a on New Zealand rabbits with normal intraocular pressure.

As shown in FIGS. 1-3, compared to the reference substance K115, compound 5 and compound 11a of the invention had a similar intraocular pressure-reducing activity and a longer acting time.

Experimental Example 4

Animal Experiment (High Intraocular Pressure Monocular Model)

10 male New Zealand rabbits were averagely divided into 2 groups and were randomly assigned to respective groups using a computer randomized algorithm involving weight. From 3 days to 1 day before the experiment, all rabbits were required to be trained to adapt to the operation of intraocular pressure (IOP) measurement, and the training was performed 3 times a day with an interval of about 3 h. The intraocular pressure was measured using a TonoVet tonometer, specifically, individual animals were fixed and the eye to be tested was placed at a position perpendicular to the TonoVet tonometer. The IOP should be measured at least 3 times in each operation until the reading became stable. The results from the last three stable measurements (±3 mmHg) were recorded and averaged to be used as the final IOP value. Respective compounds were weighed and dissolved with normal saline to the desired concentration. Before the induction of high intraocular pressure, the intraocular pressure values of both eyes were measured and used as the basic intraocular pressure value. Subsequently, individual rabbits were anesthetized by intravenous injection of (50%) 50 mg/kg sodium pentobarbital. A sharp needle 30-G was used to perform temporary paracentesis of anterior chamber. 50 µL of a viscous substance was injected into the right anterior chamber of individual rabbits to induce high intraocular pressure, and the opposite eye was injected with the same volume of normal saline. Then the anterior chamber was pressed with a cotton swab to prevent the aqueous humor from flowing back. The compound of the invention was administered to the right eye of each group of model animals three times a day respectively at the beginning, $3^{rd}$ h and $6^{th}$ h (50 µL/per eye), and the opposite eye was injected with the same volume of normal saline or a specific menstruum at the same point. The IOP was measured respectively 0, 1, 2, 3, 4, 6 and 8 h after the injection. The results obtained at individual time points were analyzed by student-t test, and the variation curve of IOP over time was analyzed using ANOVA test. A P value of less than 0.05 will be considered to be of statistical significance, and the data was expressed by mean±standard deviation.

Figure 4:
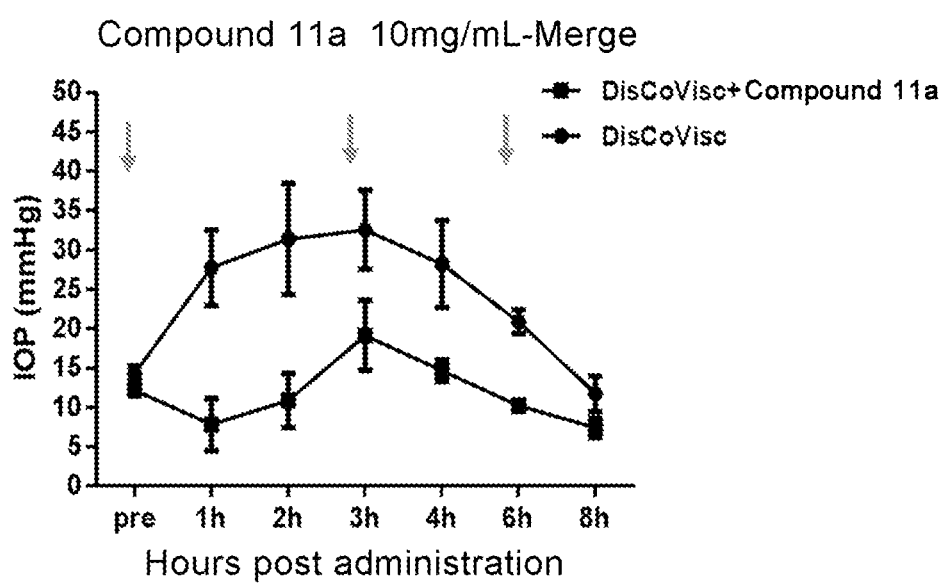
FIG. 4 shows the experimental results of the intraocular pressure-lowering activity of Compound 11a on New Zealand rabbits with high intraocular pressure.

The experimental results were shown in FIG. 4, and it can be obtained that the compound 11a showed a good effect on alleviating high intraocular pressure.

As demonstrated by the above experimental results, the compounds prepared herein had a good ROCK-inhibiting activity, so that they can be effectively applied to the treatment of diseases associated with abnormal ROCK activity.

In summary, the novel compound of formula (I) prepared herein had a good ROCK-inhibiting activity, providing a new clinical treatment for diseases associated with abnormal ROCK activity.

What is claimed is:

1. A compound of formula (II) or a stereoisomer thereof:

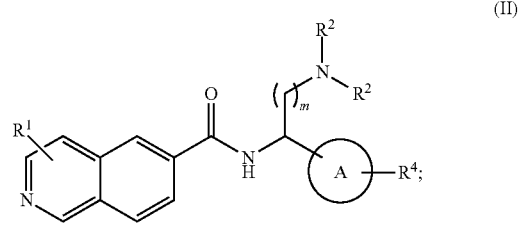

wherein:
$R^1$ is selected from the group consisting of hydrogen, hydroxyl, halogen, amino, carboxyl, trifluoromethyl, nitro, cyano and $C_1$-$C_6$ alkyl;
m is 0, 1, 2 or 3;

$R^2$ and $R^{2'}$ are independently selected from the group consisting of hydrogen and $C_1$-$C_6$ alkyl;

A ring is selected from the group consisting of 5- to 6-membered aromatic ring, 5- to 6-membered heteroaromatic ring and

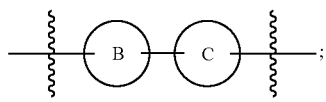

B ring and C ring are independently selected from the group consisting of 5- to 6-membered aromatic ring and 5- to 6-membered heteroaromatic ring;

$R^4$ is selected from the group consisting of hydrogen, halogen, nitro, cyano, $C_1$-$C_6$ alkyl, $C_2$-$C_6$ alkenyl, $C_2$-$C_6$ alkynyl, 3- to 6-membered cycloalkyl, 3- to 6-membered heterocycloalkyl, —$(CH_2)_mOR^a$, —$(CH_2)_mOC(O)R^a$, —$(CH_2)_mOC(O)NR^aR^b$, —$(CH_2)_mNR^aR^b$, —$(CH_2)_mNR^aC(O)R^b$, —$(CH_2)_mNR^aC(O)OR^b$, —$(CH_2)_mC(O)R^a$, —$(CH_2)_mC(O)OR^a$ and —$(CH_2)_mC(O)NR^aR^b$; and $R^a$ and $R^b$ are independently selected from the group consisting of hydrogen, $C_1$-$C_6$ alkyl, $C_2$-$C_6$ alkenyl, $C_2$-$C_6$ alkynyl, substituted and unsubstituted 3- to 6-membered cycloalkyl, substituted and unsubstituted 3- to 6-membered heterocycloalkyl, substituted and unsubstituted 5- to 6-membered aromatic ring and substituted and unsubstituted 5- to 6-membered heteroaromatic ring, wherein the substituted 3- to 6-membered cycloalkyl, substituted 3- to 6-membered heterocycloalkyl, substituted 5- to 6-membered aromatic ring and substituted 5- to 6-membered heteroaromatic ring each comprise 1-2 substituents independently selected from the group consisting of halogen and $C_1$-$C_6$ alkyl.

2. The compound of claim 1 or a stereoisomer thereof, wherein the compound is selected from the group consisting of:

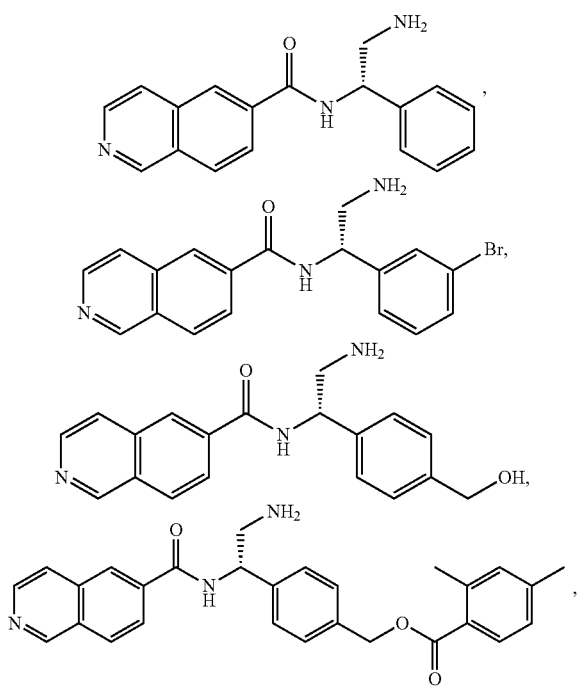

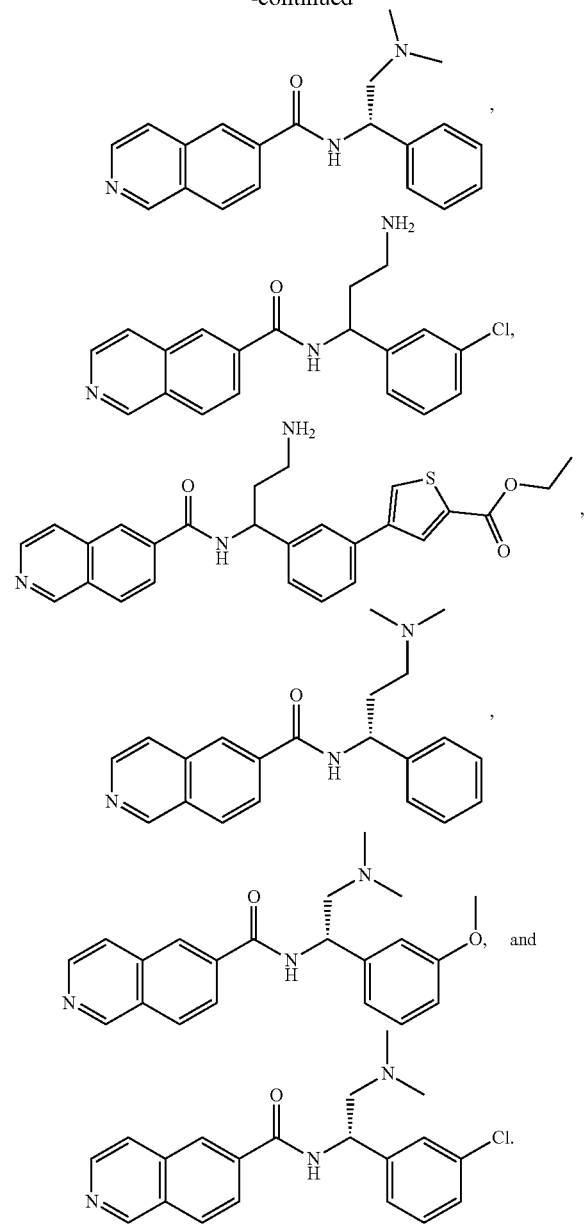

3. A compound of formula (III) or a stereoisomer thereof:

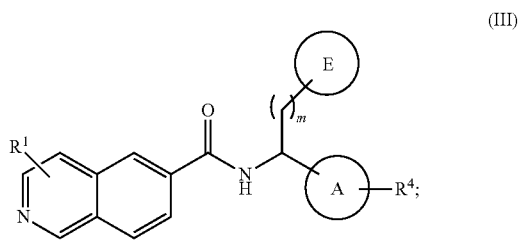

(III)

wherein $R^1$ is selected from the group consisting of hydrogen, hydroxyl, halogen, amino, carboxyl, trifluoromethyl, nitro, cyano and $C_1$-$C_6$ alkyl;

m is 0, 1, 2 or 3;

A ring is an unsubstituted phenyl;

E ring is a substituted or unsubstituted 4- to 5-membered N-containing heterocycloalkyl; wherein the substituted N-containing heterocycloalkyl comprises 1-2 substituents independently selected from the group consisting of halogen and $C_1$-$C_6$ alkyl; and $R^4$ is absent.

4. The compound of claim 3 or a stereoisomer thereof, wherein the compound is selected from the group consisting of:

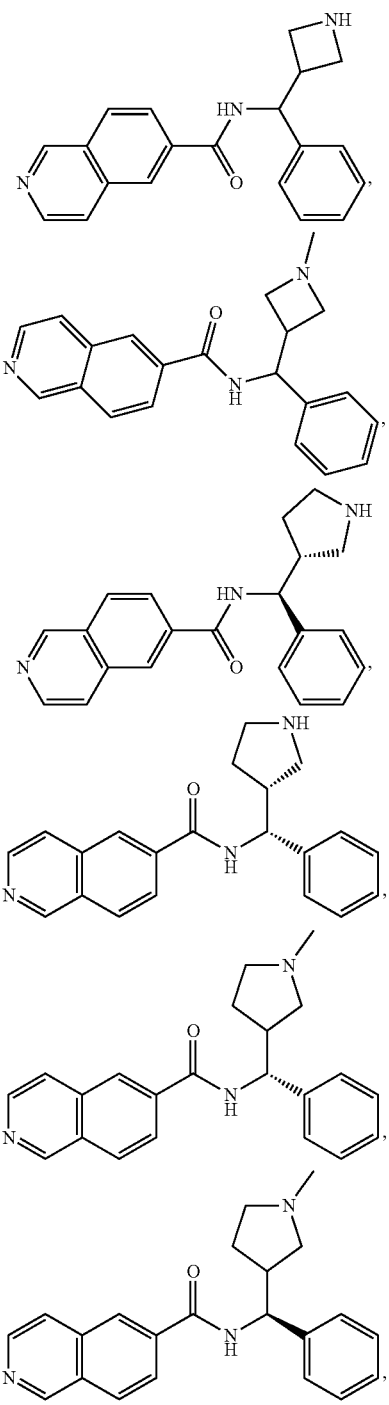

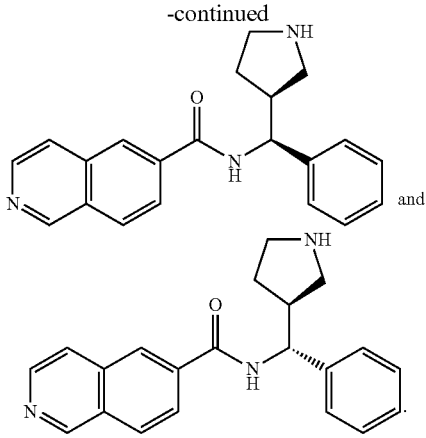

5. A method for treating a disease associated with abnormal ROCK activity in a patient in need thereof, comprising: administering an effective amount of a compound of formula (I), or a stereoisomer thereof to the patient;

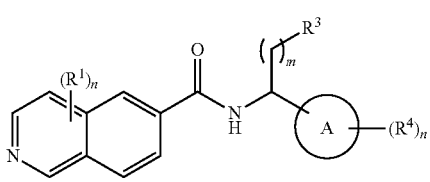

wherein:

n is independently 0, 1 or 2;

$R^1$ is independently selected from the group consisting of hydrogen, hydroxyl, halogen, amino, carboxyl, trifluoromethyl, nitro, cyano and $C_1$-$C_6$ alkyl;

m is 0, 1, 2, 3, 4 or 5;

$R^3$ is —$NR^2R^{2'}$ or a substituted or unsubstituted N-containing heterocycloalkyl, wherein the substituted N-containing heterocycloalkyl comprises 1-2 substituents independently selected from the group consisting of halogen and $C_1$-$C_6$ alkyl;

$R^2$ and $R^{2'}$ are independently hydrogen or $C_1$-$C_6$ alkyl;

A ring is selected from the group consisting of 5- to 6-membered aromatic ring, 5- to 6-membered heteroaromatic ring and

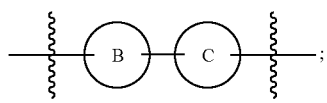

wherein B ring and C ring are independently selected from the group consisting of 5- to 6-membered aromatic ring and 5- to 6-membered heteroaromatic ring;

$R^4$ is independently selected from the group consisting of hydrogen, halogen, nitro, cyano, $C_1$-$C_6$ alkyl, $C_2$-$C_6$ alkenyl, $C_2$-$C_6$ alkynyl, 3- to 6-membered cycloalkyl, 3- to 6-membered heterocycloalkyl, —$(CH_2)_mOR^a$, —$(CH_2)_mOC(O)R^a$, —$(CH_2)_mOC(O)NR^aR^b$, —$(CH_2)_mNR^aR^b$, —$(CH_2)_mNR^aC(O)R^b$, —$(CH_2)_mNR^aC(O)OR^b$, —$(CH_2)_mC(O)R^a$, —$(CH_2)_mC(O)OR^a$ and —$(CH_2)_mC(O)NR^aR^b$; and $R^a$ and $R^b$ are independently selected from the group consisting of hydrogen, $C_1$-$C_6$ alkyl, $C_2$-$C_6$ alkenyl, $C_2$-$C_6$ alkynyl, substituted and unsubstituted 3- to 6-membered cycloalkyl, substituted and unsubstituted 3- to 6-membered heterocycloalkyl, substituted and unsubstituted 5- to 6-membered aromatic ring and substituted and unsubstituted 5- to 6-membered heteroaromatic ring, wherein the substituted 3- to 6-membered cycloalkyl, substituted 3- to 6-membered heterocycloalkyl, substituted 5- to 6-membered aromatic ring and substituted 5- to 6-membered heteroaromatic ring each comprise 1-2 substituents independently selected from the group consisting of halogen and $C_1$-$C_6$ alkyl.

6. The method of claim 5, wherein the disease associated with abnormal ROCK activity is associated with cytoskeleton regulation, smooth muscle contraction and nerve regeneration.

7. The method of claim 6, wherein the disease associated with abnormal ROCK activity is ocular hypertension or glaucoma.

8. A pharmaceutical composition, comprising the compound of claim 1, or a stereoisomer thereof as an active ingredient and a pharmaceutically-acceptable adjuvant.

9. A pharmaceutical composition, comprising the compound of claim 3, or a stereoisomer thereof as an active ingredient and a pharmaceutically-acceptable adjuvant.

\* \* \* \* \*